US008048012B1

(12) United States Patent
Castro

(10) Patent No.: US 8,048,012 B1
(45) Date of Patent: Nov. 1, 2011

(54) ARTICULATED CUSTOM ANKLE-FOOT ORTHOSIS SYSTEMS

(76) Inventor: Ernesto G. Castro, Mesa, AZ (US)

( * ) Notice: Subject to any disclaimer, the term of this patent is extended or adjusted under 35 U.S.C. 154(b) by 0 days.

(21) Appl. No.: 12/708,434

(22) Filed: Feb. 18, 2010

Related U.S. Application Data

(63) Continuation-in-part of application No. 10/968,603, filed on Oct. 18, 2004, now Pat. No. 7,691,076.

(60) Provisional application No. 60/515,608, filed on Oct. 29, 2003, provisional application No. 60/554,223, filed on Mar. 17, 2004.

(51) Int. Cl.
*A61F 5/00* (2006.01)
(52) U.S. Cl. ............................... 602/23; 602/27
(58) Field of Classification Search .............. 602/23–28, 602/60–62; 128/882; 2/22, 911, 919; 36/1, 36/1.5, 83, 140
See application file for complete search history.

(56) References Cited

U.S. PATENT DOCUMENTS

| 4,289,122 | A | | 9/1981 | Mason et al. | |
|---|---|---|---|---|---|
| 4,825,856 | A | | 5/1989 | Nelson | |
| 4,834,078 | A | * | 5/1989 | Biedermann | 602/27 |
| 5,086,760 | A | | 2/1992 | Neumann et al. | |
| 5,143,058 | A | * | 9/1992 | Luber et al. | 602/28 |
| 5,372,576 | A | * | 12/1994 | Hicks | 602/27 |
| 5,961,477 | A | * | 10/1999 | Turtzo | 602/27 |
| 6,056,712 | A | | 5/2000 | Grim | |
| 6,056,713 | A | * | 5/2000 | Hayashi | 602/27 |
| 6,155,997 | A | | 12/2000 | Castro | |
| 6,443,919 | B1 | | 9/2002 | Castro | |
| 6,866,043 | B1 | * | 3/2005 | Davis | 128/842 |

FOREIGN PATENT DOCUMENTS

CA 2276344 7/1998

* cited by examiner

*Primary Examiner* — Michael A. Brown
(74) *Attorney, Agent, or Firm* — Stoneman Law Patent Group; Martin L. Stoneman

(57) ABSTRACT

A custom articulated ankle-foot orthosis (AFO) system is disclosed that is formed on a cast of the wearer's foot. The custom articulated AFO has an adjustably tightenable calf section hingedly connected to an adjustably tightenable foot section. The custom articulated AFO is made of thermally formable plastic sheet, is lined inside and outside, and is padded inside. The brace permits dorsal/plantar flexion while supporting the ankle against supination and pronation. The apparatus and methods of manufacture are disclosed.

19 Claims, 18 Drawing Sheets

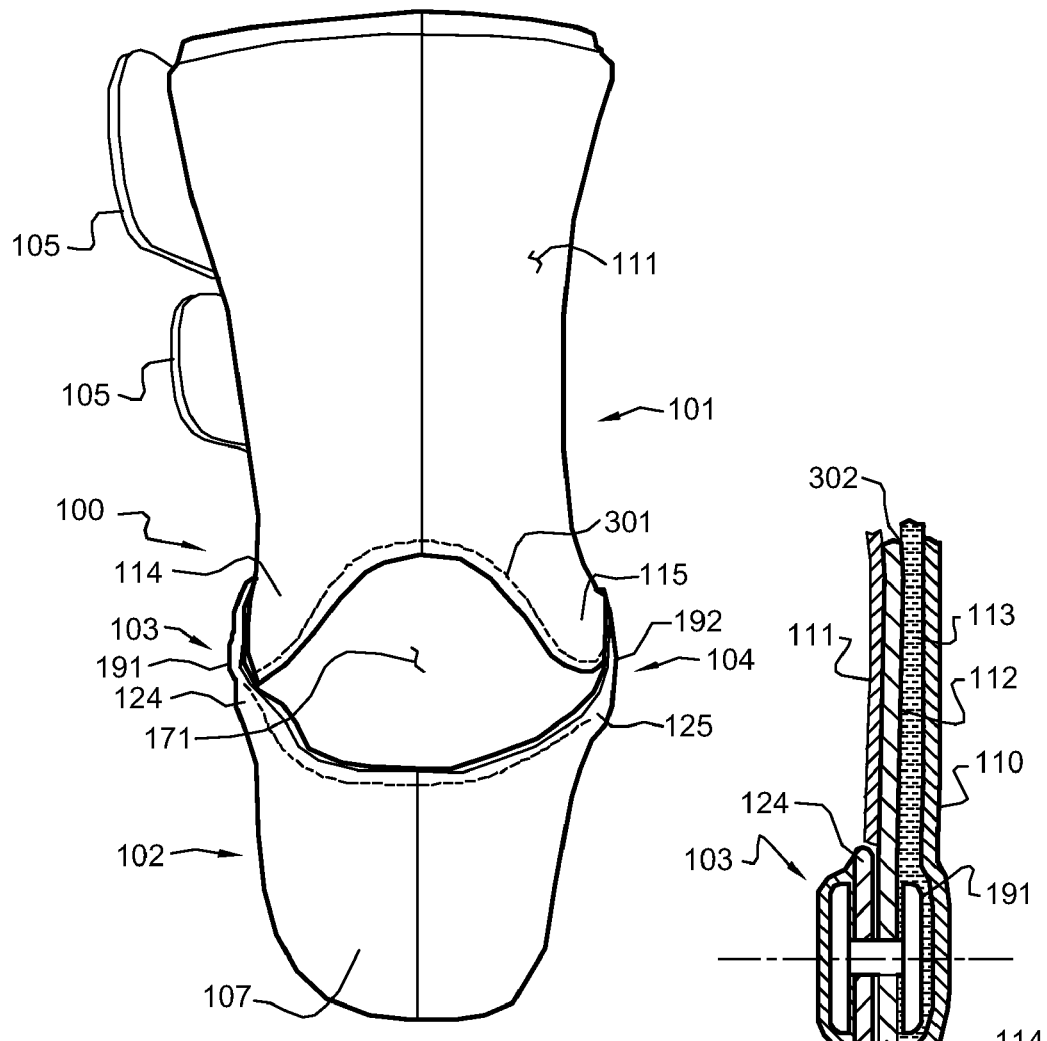
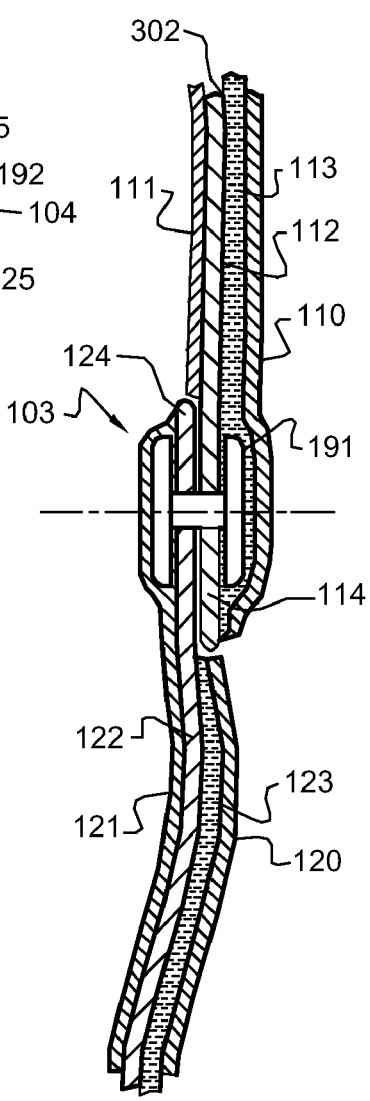
FIG. 3
FIG. 4

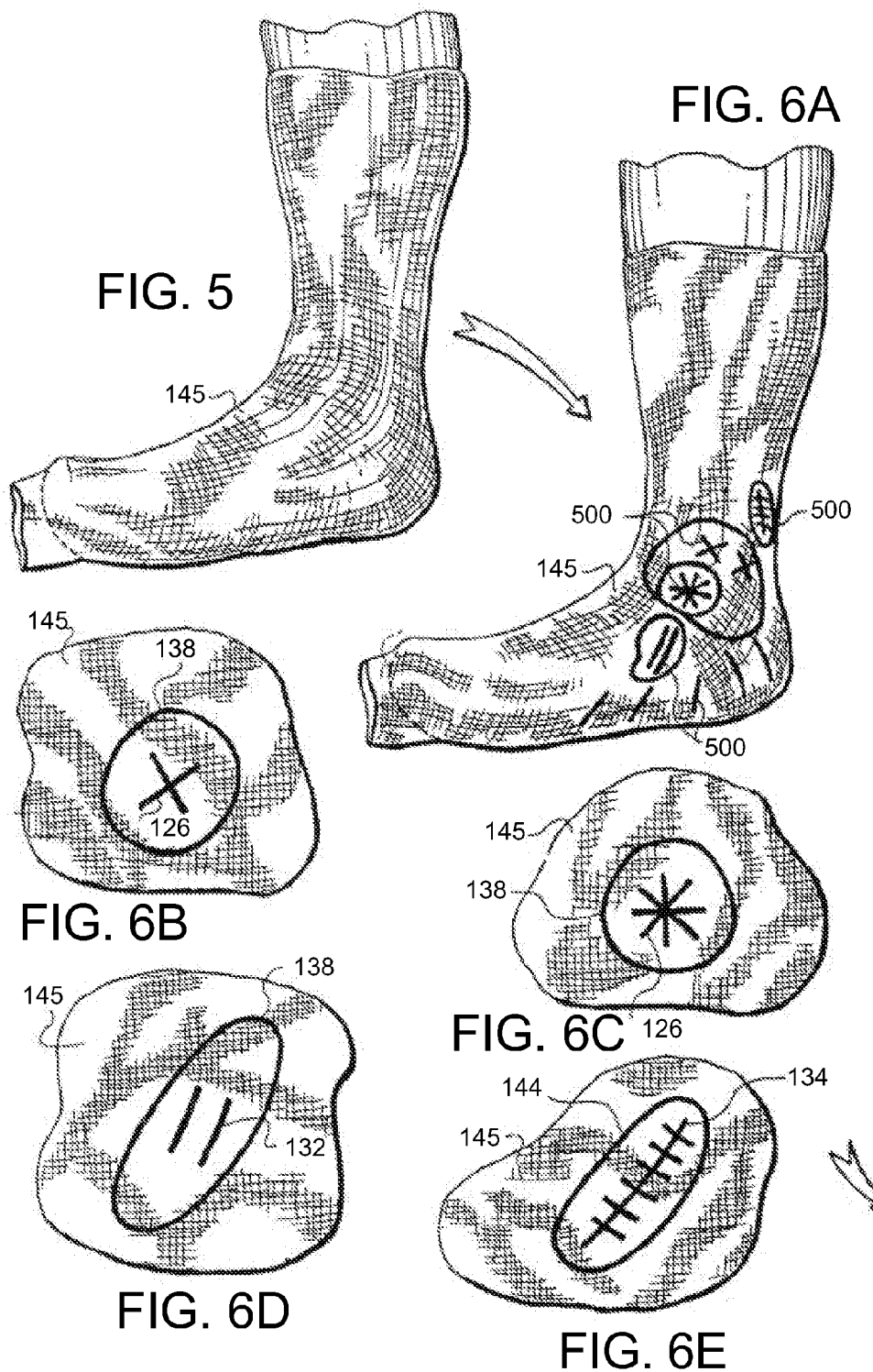

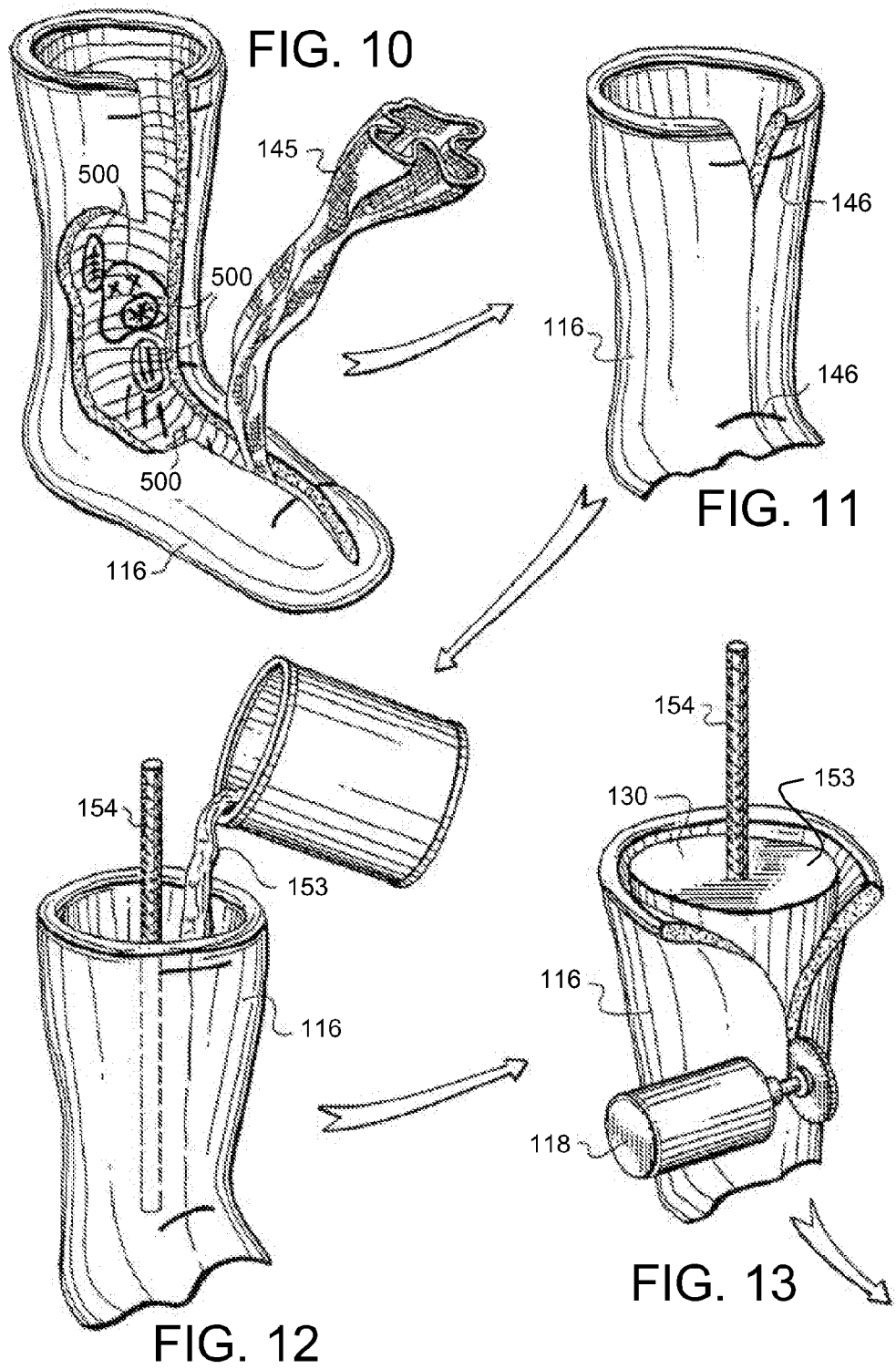

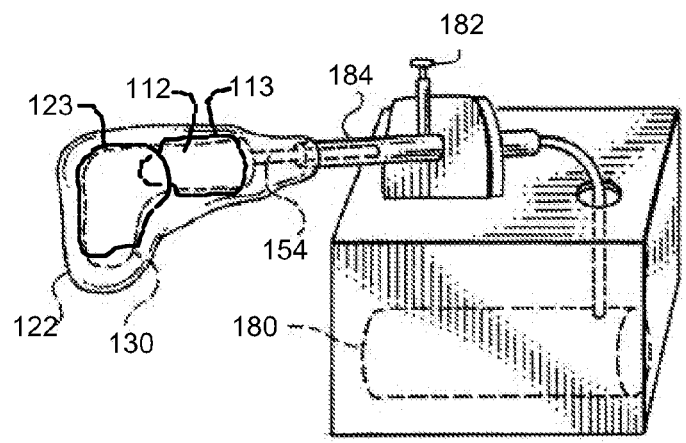
FIG. 20
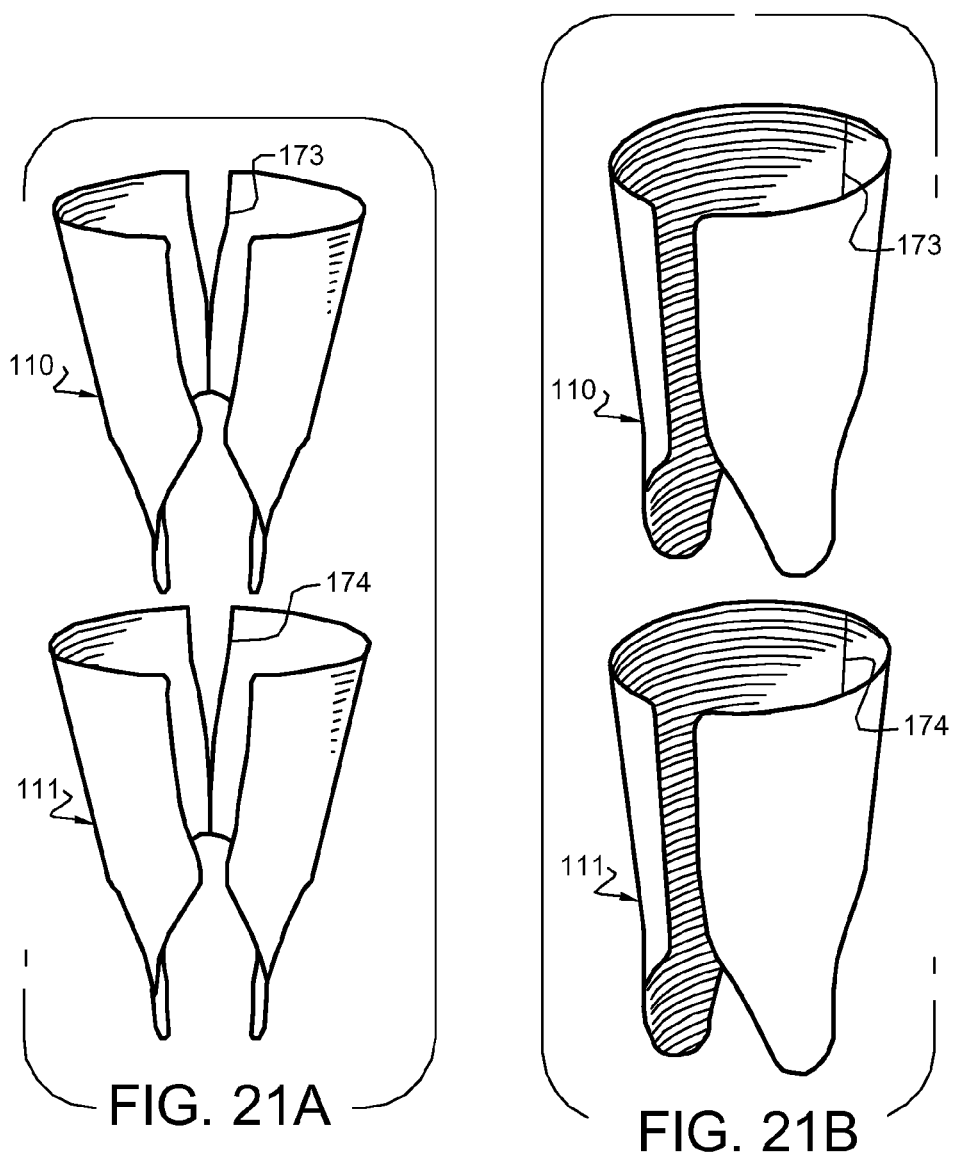
FIG. 21A
FIG. 21B

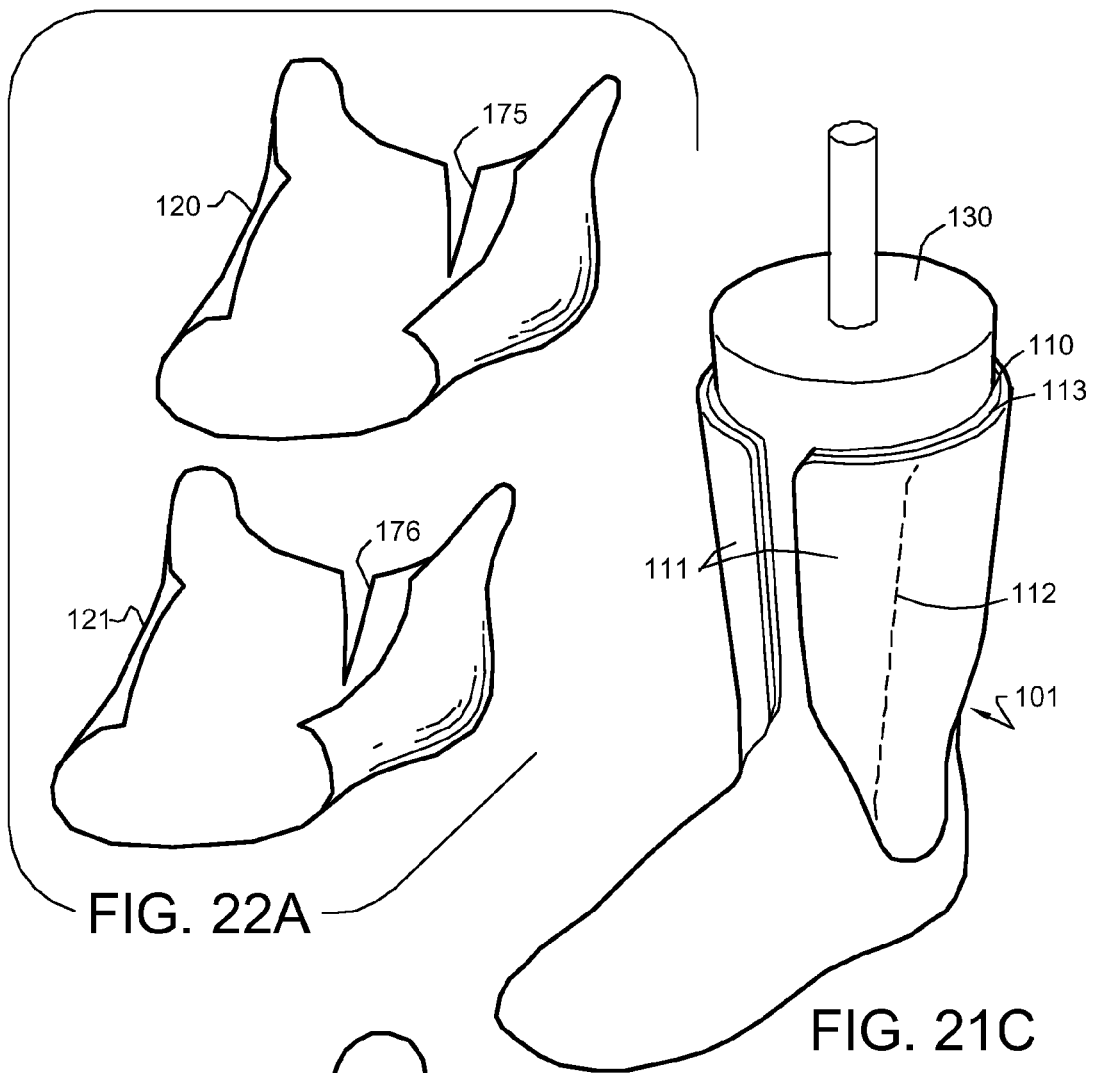
FIG. 22A
FIG. 21C
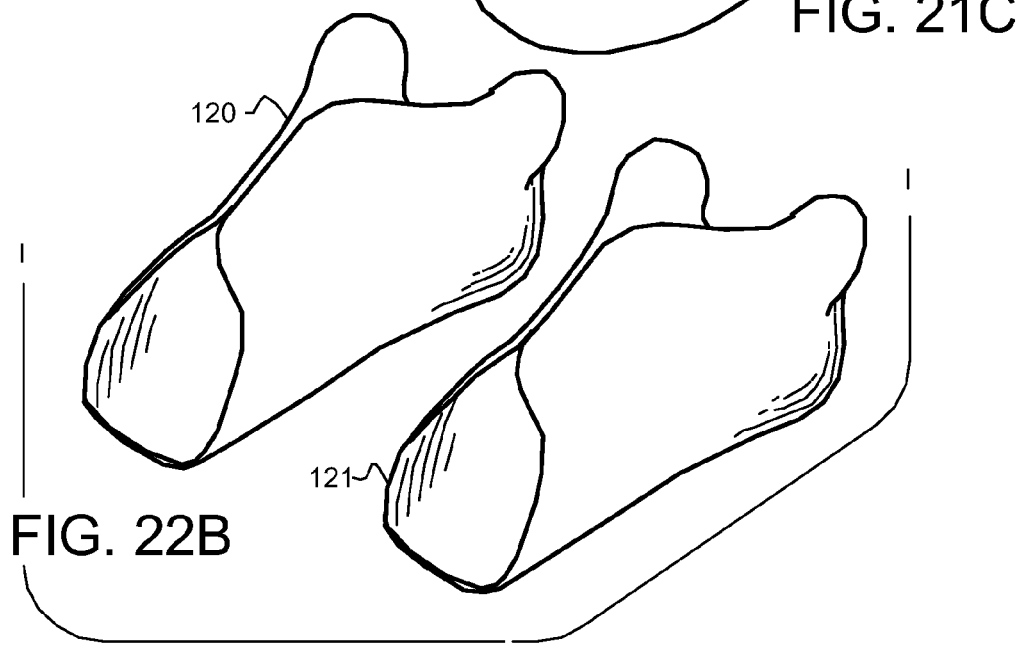
FIG. 22B

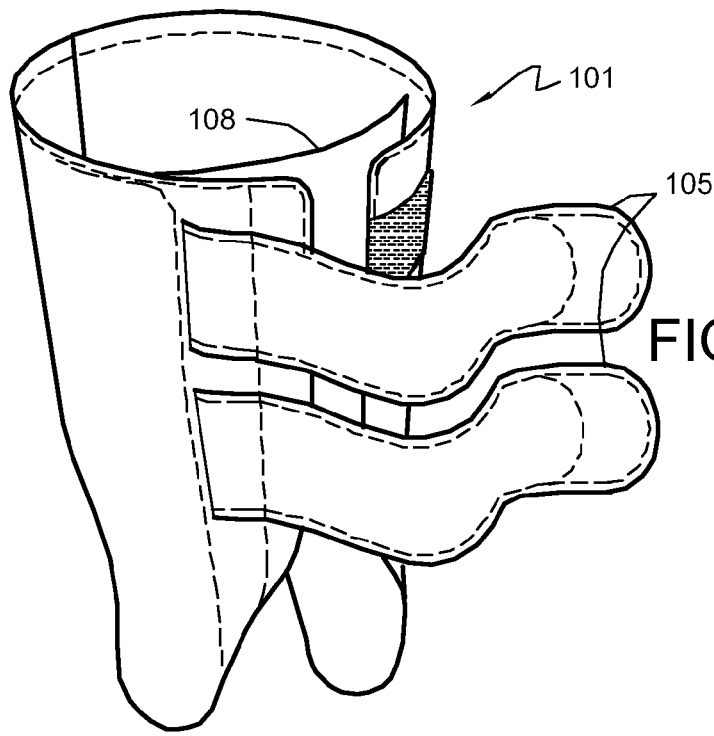
FIG. 23
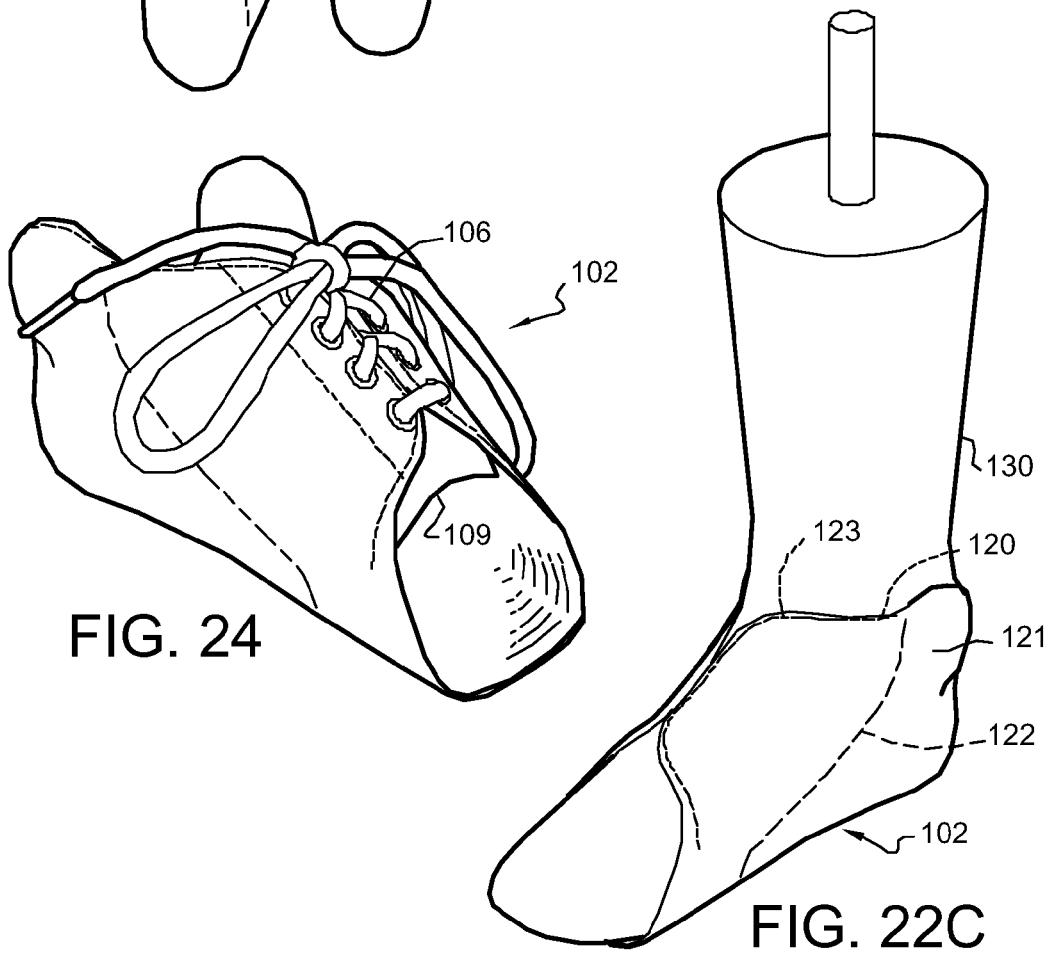
FIG. 24
FIG. 22C

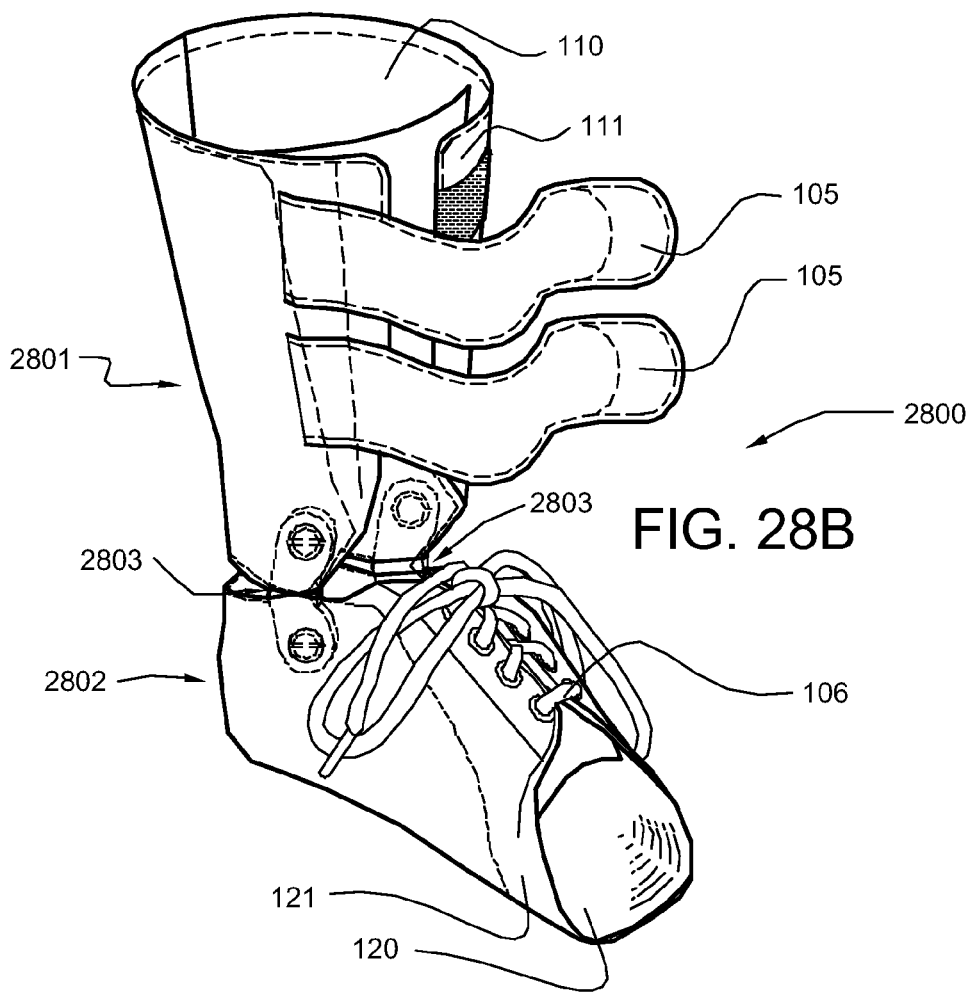
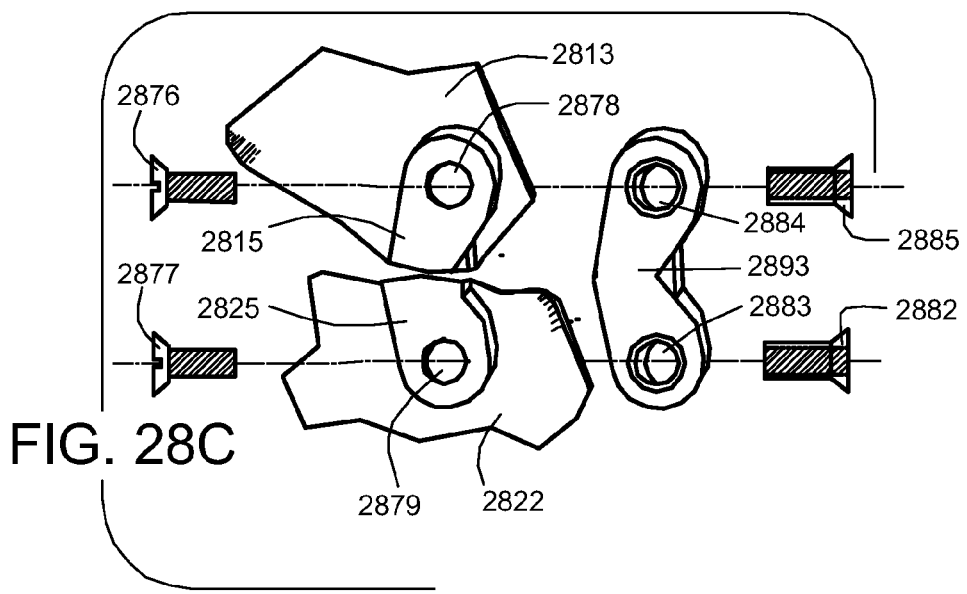

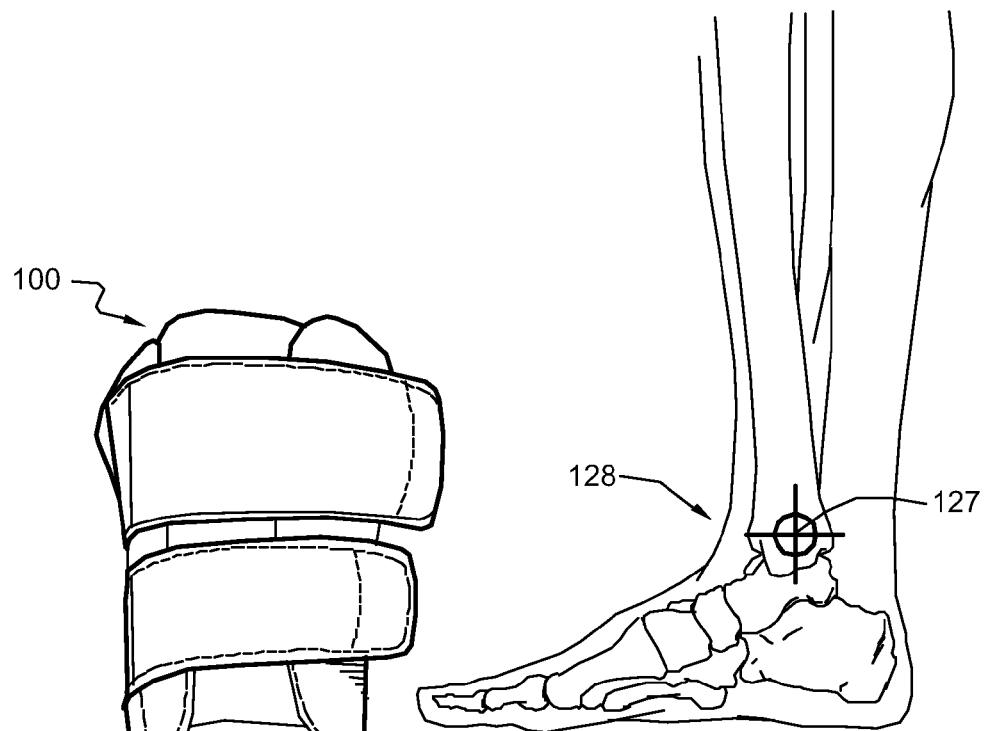
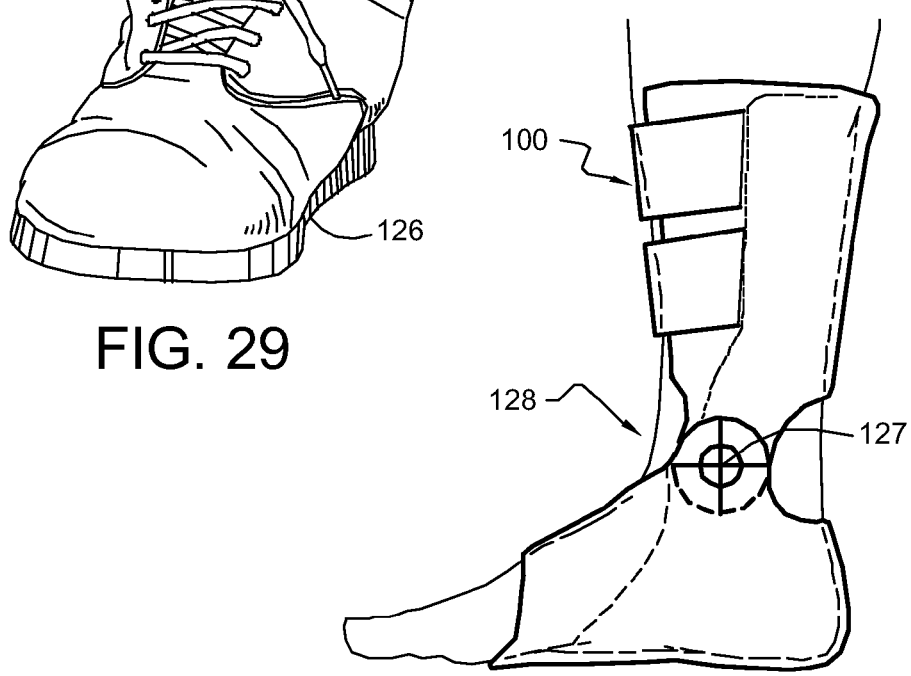
FIG. 29
FIG. 30A
FIG. 30B

ARTICULATED CUSTOM ANKLE-FOOT ORTHOSIS SYSTEMS

CROSS-REFERENCE TO RELATED APPLICATIONS

The present application is a continuation-in-part and is related to and claims priority from application Ser. No. 10/968,603, filed Oct. 18, 2004, entitled "ARTICULATED CUSTOM ANKLE-FOOT ORTHOSIS SYSTEM", which application is related to and claims priority from prior provisional application Ser. No. 60/515,608, filed Oct. 29, 2003, entitled "ARTICULATED CUSTOM ANKLE-FOOT ORTHOSIS SYSTEM", and is related to and claims priority from prior provisional application Ser. No. 60/554,223, filed Mar. 17, 2004, entitled "ARTICULATED CUSTOM ANKLE-FOOT ORTHOSIS SYSTEM", the contents of all of which are incorporated herein by this reference and are not admitted to be prior art with respect to the present invention by the mention in this cross-reference section.

BACKGROUND

Typically, individuals suffer from certain conditions of the feet that either greatly limit unaided mobility or require the use of aids such as walkers or canes in order for the individual to be mobile. Conditions which may cause this debilitating condition include tibialis tendonitis or rupture, degenerate joint disease, talocalcaneal varus or valgus, severe pronation, and/or trauma to ankle, talocalcaneal, subtalar, or midtarsal joints. To treat these conditions necessarily requires a stabilizing-type apparatus in order to stabilize the ankle area, talocalcaneal, midtarsal, and subtalar joints so that medial and lateral stability of the foot is achieved with the result that the patient enjoys the benefits of greater mobility.

Generally, the braces used for these types of ailments are large, thick, cumbersome, unattractive, and expensive. The patient must purchase a shoe or shoes that are one or many shoe sizes larger than they would normally require and must pay the expense of having a shoe made from a casting of their foot. Furthermore, less expensive, over-the-counter ankle braces do not provide adequate support and chafe sensitive areas of the feet that do not conform to the off-the-shelf brace.

In many cases of moderate or slight severity, it is desirable to affect medial (inner ankle) and lateral (outer ankle) stabilization while still permitting dorsal (upward) and plantar (downward) flexion of the foot. This permits the patient to walk more normally while still protecting the ankle joints from supination (where the ankle rolls outward) and pronation (where the ankle rolls inward). This may be accomplished by placing a hinge in the ankle-foot orthosis in line with the natural dorsal and plantar flexion of the ankle, creating an articulated ankle-foot orthosis or brace. Such hinges are typically not covered, and snag clothing and other objects.

Therefore, a need exists for an articulated AFO that is attractive, comfortable, fits in a normal-sized shoe, and does not snag clothing.

OBJECTS AND FEATURES OF THE INVENTION

A primary object and feature of the present invention is to provide articulated custom AFO systems overcoming the above-stated problems. It is a further object and feature of the present invention to provide such an articulated custom AFO system that is efficient and permits the patient to wear essentially normal shoes. Yet another object and feature of the present invention is to provide a padded, lined, and covered articulated custom AFO system. Also, it is an object and feature of this invention to provide an articulated custom AFO system with a lined and padded hinge. In addition, it is a primary object and feature of this invention to provide such an articulated custom AFO system in connection with, and making use of, a novel articulated custom AFO. Furthermore, it is an object and feature of this invention to provide methods of manufacturing a novel articulated custom AFO.

Other objects and features of this invention will become apparent with reference to the following descriptions.

SUMMARY OF THE INVENTION

In accordance with a preferred embodiment hereof, this invention provides an articulated custom AFO system, for permitting dorsal and plantar ankle flexion between a calf and a foot of at least one user, comprising: at least one calf portion, having inside and outside surfaces; at least one foot portion, having inside and outside surfaces; calf stiffener means, having medial and lateral sides and inside and outside surfaces, for stiffly supporting such at least one calf portion; foot stiffener means, having medial and lateral sides and inside and outside surfaces, for stiffly supporting such at least one foot portion; medial hinge means for hingedly connecting such medial side of such calf stiffener means to such medial side of such foot stiffener means; lateral hinge means for hingedly connecting such lateral side of such calf stiffener means to such lateral side of such foot stiffener means; calf outer lining means for pliably lining at least such outside surface of such calf stiffener means; foot outer lining means for pliably lining at least such outside surface of such foot stiffener means; calf tightener means for tightening such calf outer lining means about the calf of the at least one user; and attachment means for attaching such calf tightener means with such calf outer lining means.

Moreover, it provides such an articulated custom AFO system, further comprising attachment means for attaching such calf stiffener means with such calf outer lining means. Additionally, it provides such an articulated custom AFO system, further comprising attachment means for attaching such foot stiffener means with such foot outer lining means. Also, it provides such an articulated custom AFO system, further comprising foot inner lining means for pliably lining at least such inside surface of such at least one foot portion. In addition, it provides such an articulated custom AFO system, further comprising calf inner lining means for pliably lining at least such inside surface of such at least one calf portion. And, it provides such an articulated custom AFO system, further comprising calf padding means for padding at least substantially such inner surface of such calf stiffener means.

Further, it provides such an articulated custom AFO system, further comprising foot padding means for padding at least substantially such inner surface of such foot stiffener means. Even further, it provides such an articulated custom AFO system, further comprising foot tightener means for tightening such foot outer lining means about the foot of the at least one user. Moreover, it provides such an articulated custom AFO system, further comprising calf tongue means for covering the area at least under such calf tightener means. Additionally, it provides such an articulated custom AFO system, further comprising foot tongue means for covering the area at least under such foot tightener means.

Also, it provides such an articulated custom AFO system, further comprising backstop means for stopping such foot portion from moving past a certain angle relative to such calf portion. In addition, it provides such an articulated custom AFO system, wherein such foot outer lining means substantially covers the outer surfaces of such medial hinge means and such lateral hinge means.

In accordance with another preferred embodiment hereof, this invention provides an articulated custom AFO system, for permitting dorsal and plantar ankle flexion between a calf and a foot of at least one user, comprising: at least one calf portion, having inside and outside surfaces; at least one foot portion, having inside and outside surfaces; at least one calf stiffener, having medial and lateral sides and inside and outside surfaces, structured and arranged to stiffly support such at least one calf portion; at least one foot stiffener, having medial and lateral sides and inside and outside surfaces, structured and arranged to stiffly support such at least one foot portion; at least one medial hinge structured and arranged to hingedly connect such medial side of such at least one calf stiffener to such medial side of such at least one foot stiffener; at least one lateral hinge structured and arranged to hingedly connect such lateral side of such at least one calf stiffener to such lateral side of such at least one foot stiffener; at least one calf outer lining structured and arranged to pliably line at least such outside surface of such at least one calf stiffener; at least one foot outer lining structured and arranged to pliably line at least such outside surface of such at least one foot stiffener; at least one calf tightener structured and arranged to tighten such at least one calf outer lining about the calf of the at least one user; and at least one attacher structured and arranged to attach such at least one calf tightener with such at least one calf outer lining.

And, it provides such an articulated custom AFO system, wherein such at least one attacher structured and arranged to attach such at least one calf tightener with such at least one calf outer lining comprises at least one adhesive. Further, it provides such an articulated custom AFO system, further comprising at least one attacher structured and arranged to attach such at least one foot stiffener with such at least one foot outer liner. Even further, it provides such an articulated custom AFO system, wherein such at least one attacher structured and arranged to attach such at least one foot stiffener with such at least one foot outer liner comprises at least one adhesive. Moreover, it provides such an articulated custom AFO system, further comprising at least one foot inner liner structured and arranged to pliably line at least such at least one inside surface of such at least one foot portion.

Additionally, it provides such an articulated custom AFO system, further comprising at least one attacher structured and arranged to attach such at least one calf stiffener with such at least one calf outer liner. Also, it provides such an articulated custom AFO system, wherein such at least one attacher structured and arranged to attach such at least one calf stiffener with such at least one calf outer liner comprises at least one adhesive. In addition, it provides such an articulated custom AFO system, further comprising at least one attacher structured and arranged to attach such at least one foot stiffener with such at least one foot outer liner. And, it provides such an articulated custom AFO system, wherein such at least one attacher structured and arranged to attach such at least one foot stiffener with such at least one foot outer liner comprises at least one adhesive. Further, it provides such an articulated custom AFO system, further comprising at least one foot inner liner structured and arranged to pliably line at least such at least one inside surface of such at least one foot portion. Even further, it provides such an articulated custom AFO system, wherein such at least one foot inner liner comprises at least one leather. Moreover, it provides such an articulated custom AFO system, further comprising at least one calf inner liner structured and arranged to pliably line at least such at least one inside surface of such at least one calf portion. Additionally, it provides such an articulated custom AFO system, wherein such at least one calf inner liner comprises at least one leather.

Also, it provides such an articulated custom AFO system, further comprising at least one foot tightener structured and arranged to tighten such at least one foot outer liner about the foot of the at least one user. In addition, it provides such an articulated custom AFO system, wherein such at least one foot tightener comprises at least one grommet and at least one lace. And, it provides such an articulated custom AFO system, further comprising at least one calf tongue structured and arranged to cover the area at least under such at least one calf tightener. Further, it provides such an articulated custom AFO system, wherein such at least one calf tongue comprises at least one leather.

Even further, it provides such an articulated custom AFO system, further comprising at least one foot tongue structured and arranged to cover the area at least under such at least one foot tightener. Moreover, it provides such an articulated custom AFO system, wherein such at least one foot tongue comprises at least one leather. Additionally, it provides such an articulated custom AFO system, further comprising at least one calf pad structured and arranged to pad at least substantially such at least one inner surface of such at least one calf stiffener means. Also, it provides such an articulated custom AFO system, wherein such at least one calf pad comprises at least one low-temperature thermoplastic foam. In addition, it provides such an articulated custom AFO system, further comprising at least one foot pad structured and arranged to pad at least substantially such at least one inner surface of such at least one foot stiffener means. And, it provides such an articulated custom AFO system, wherein such at least one foot pad comprises at least one low-temperature thermoplastic foam. Further, it provides such an articulated custom AFO system, wherein such at least one foot outer liner substantially covers the outer surfaces of such at least one medial hinge and such at least one lateral hinge. Even further, it provides such an articulated custom AFO system, wherein such at least one calf stiffener comprises at least one low-temperature thermoplastic. Moreover, it provides such an articulated custom AFO system, wherein such at least one foot stiffener comprises at least one low-temperature thermoplastic.

Additionally, it provides such an articulated custom AFO system, wherein such at least one lateral hinge comprises at least one rivet hinge. Also, it provides such an articulated custom AFO system, wherein such at least one lateral hinge comprises at least one pre-made ankle hinge. In addition, it provides such an articulated custom AFO system, wherein such at least one pre-made ankle hinge comprises at least one TAMARACK® brand hinge. And, it provides such an articulated custom AFO system, wherein such at least one pre-made ankle hinge comprises at least one MASSER® brand hinge. Further, it provides such an articulated custom AFO system, wherein such at least one pre-made ankle hinge comprises at least one GAFFNEY® brand hinge. Even further, it provides such an articulated custom AFO system, wherein such at least one medial hinge comprises at least one rivet hinge. Moreover, it provides such an articulated custom AFO system, wherein such at least one medial hinge comprises at least one pre-made medial ankle hinge. Additionally, it provides such an articulated custom AFO system, wherein such at least one premade medial ankle hinge comprises at least one TAMARACK® brand hinge. Also, it provides such an articulated custom AFO system, wherein such at least one premade medial ankle hinge comprises at least one MASSER® brand hinge. In addition, it provides such an articulated custom AFO system, wherein such at least one premade medial ankle hinge comprises at least one GAFFNEY® brand hinge.

And, it provides such an articulated custom AFO system, wherein such at least one calf outer lining comprises at least one leather. Further, it provides such an articulated custom AFO system, wherein such at least one foot outer lining comprises at least one leather. Even further, it provides such an articulated custom AFO system, wherein such at least one attacher comprises at least one stitch. Moreover, it provides such an articulated custom AFO system, wherein such at least one calf tightener comprises at least one hook and loop fastener. Additionally, it provides such an articulated custom AFO system, further comprising at least one backstop structured and arranged to stop such at least one foot portion from moving past at least one angle relative to such at least one calf portion.

In accordance with another preferred embodiment hereof, this invention provides an articulated custom AFO system, for permitting dorsal and plantar ankle flexion between a calf and a foot of at least one user, comprising: at least one calf portion, having inside and outside surfaces; at least one foot portion, having inside and outside surfaces; at least one calf stiffener, having medial and lateral sides and inside and outside surfaces, structured and arranged to stiffly support such at least one calf portion; at least one foot stiffener, having medial and lateral sides and inside and outside surfaces, structured and arranged to stiffly support such at least one foot portion; at least one medial hinge structured and arranged to hingedly connect such medial side of such at least one calf stiffener to such medial side of such at least one foot stiffener; at least one lateral hinge structured and arranged to hingedly connect such lateral side of such at least one calf stiffener to such lateral side of such at least one foot stiffener; at least one calf outer lining structured and arranged to pliably line at least such outside surface of such at least one calf stiffener; at least one foot outer lining structured and arranged to pliably line at least such outside surface of such at least one foot stiffener; at least one foot tightener structured and arranged to tighten such at least one foot outer lining about the foot of the at least one user; and at least one attacher structured and arranged to attach such at least one foot tightener with such at least one foot outer lining. Also, it provides such an articulated custom AFO system, further comprising at least one backstop structured and arranged to stop such at least one foot portion from moving past at least one angle relative to such at least one calf portion. In addition, it provides such an articulated custom AFO system, wherein such at least one foot tightener comprises at least one grommet and at least one lace.

In accordance with another preferred embodiment hereof, this invention provides a method of making at least one custom articulated custom AFO system, for permitting dorsal and plantar ankle flexion between a calf and a foot of a lower leg of at least one user, comprising the steps of: making at least one custom articulated AFO; making at least one outer calf lining; making at least one outer foot lining; attaching such at least one calf outer lining to such at least one custom articulated AFO; and attaching such at least one foot outer lining to such at least one custom articulated AFO.

In accordance with another preferred embodiment hereof, this invention provides a method of making at least one custom articulated custom AFO system, using at least one positive cast of a foot and lower leg of a patient, at least one ankle-foot orthosis, articulated to permit dorsal and plantar ankle flexion, comprising the steps of: making at least one build-up of such at least one positive cast; making at least one build-up of such at least one positive cast to provide for the placement of at least one medial hinge and at least one lateral hinge; making at least one support brace pattern from such at least one positive cast; making at least one material layers to fit such at least one support brace pattern; using such at least one positive cast, making at least one calf stiffener for use within such at least one material layers in making such at least one ankle-foot orthosis for such patient; wherein such at least one calf stiffener is conformable to such at least one positive cast when heated; using such at least one positive cast, making at least one foot stiffener for use within such at least one material layers in making such at least one ankle-foot orthosis for such patient; wherein such at least one foot stiffener is conformable to such at least one positive cast when heated; attaching such at least one material layers to such at least one calf stiffener and at least one foot stiffener; attaching such at least one medial hinge and at least one lateral hinge to such at least one calf stiffener and such at least one foot stiffener; wherein such at least one material layers substantially cover such at least one medial hinge and such at least one lateral hinge; attaching at least one tightener; attaching at least one tongue; and trimming and finishing such at least one articulated custom AFO system.

In accordance with another preferred embodiment hereof, this invention provides a method of making at least one custom articulated custom AFO system, using at least one positive cast of a foot and lower leg of a patient, at least one ankle-foot orthosis, articulated to permit dorsal and plantar ankle flexion, comprising the steps of: making at least one build-up of such at least one positive cast; making at least one support brace pattern from such at least one positive cast; making at least one material layers to fit such at least one support brace pattern; using such at least one positive cast, making at least one brace stiffener for use within such at least one material layers in making such at least one ankle-foot orthosis for such patient; wherein such at least one brace stiffener is conformable to such at least one positive cast when heated; cutting such at least one brace stiffener to make at least one calf stiffener and at least one foot stiffener; attaching such at least one material layers to such at least one calf stiffener and at least one foot stiffener; attaching such at least one medial hinge and at least one lateral hinge to such at least one calf stiffener and such at least one foot stiffener; wherein such at least one material layers substantially cover such at least one medial hinge and such at least one lateral hinge; attaching at least one tightener; attaching at least one tongue; and trimming and finishing such at least one articulated custom AFO system.

And, it provides such a method, further comprising the step of making at least one build-up of such at least one positive cast to provide for the placement of such at least one medial hinge and such at least one lateral hinge. Further, it provides such a method, further comprising the step of placing at least one molding dummy on such at least one positive cast to provide for the placement of such at least one medial hinge and such at least one lateral hinge. Even further, it provides such a method, further comprising the step of stamping such at least one calf stiffener and such at least one foot stiffener to provide for the placement of such at least one medial hinge and such at least one lateral hinge.

Further, this invention provides each and every novel feature, element, combination, step and/or method disclosed or suggested by this patent application.

BRIEF DESCRIPTION OF THE DRAWINGS

FIG. 3 is a rear view of the articulated custom AFO system of FIG. 1.

FIG. 4 is a rear cross sectional view through the section 4-4 of FIG. 1.

FIG. 5 illustrates a cotton stockinette placed on the foot of a patient.

FIG. 6A shows transferable diagnostic markings placed on the stockinette.

FIG. 6B illustrates preferred diagnostic indicia.

FIG. 6C illustrates preferred diagnostic indicia.

FIG. 6D illustrates preferred diagnostic indicia.

FIG. 6E illustrates preferred diagnostic indicia.

FIG. 10 shows the stockinette being removed from the negative cast.

FIG. 11 shows the negative cast being sealed prior to making a positive cast.

FIG. 12 shows filling the negative cast with plaster and a rebar.

FIG. 13 shows removing the negative cast from the positive cast.

FIG. 20 shows the process of vacuum thermoforming second sheets of thermoformable plastic and foam over the positive cast and the trimmed calf section.

FIG. 21A shows the leather lining pieces for the calf section.

FIG. 21B shows the sewn leather lining pieces for the calf section.

FIG. 21C shows the leather lining pieces glued and sewn to the calf stiffener and calf pad.

FIG. 22A shows the leather lining pieces for the foot section.

FIG. 22B shows the sewn leather lining pieces for the foot section.

FIG. 22C shows the leather lining pieces glued and sewn to the foot stiffener and foot pad.

FIG. 23 shows the calf section with tongue and tighteners attached.

FIG. 24 shows the foot section with tongue and tighteners attached.

FIG. 28B shows the completed articulated custom AFO system according to FIG. 28A with preferred hinges installed.

FIG. 28C shows an exploded view of the preferred hinges of the articulated custom AFO system according to FIG. 28B.

FIG. 29 shows the completed articulated custom AFO system with an essentially normal shoe.

FIG. 30A shows the plantar/dorsal pivot point of an ankle

FIG. 30B shows the plantar/dorsal pivot point of the completed articulated custom AFO system, which aligns with the plantar/dorsal pivot point of an ankle.

DETAILED DESCRIPTION OF THE BEST MODES AND PREFERRED EMBODIMENTS OF THE INVENTION

Figure 1:
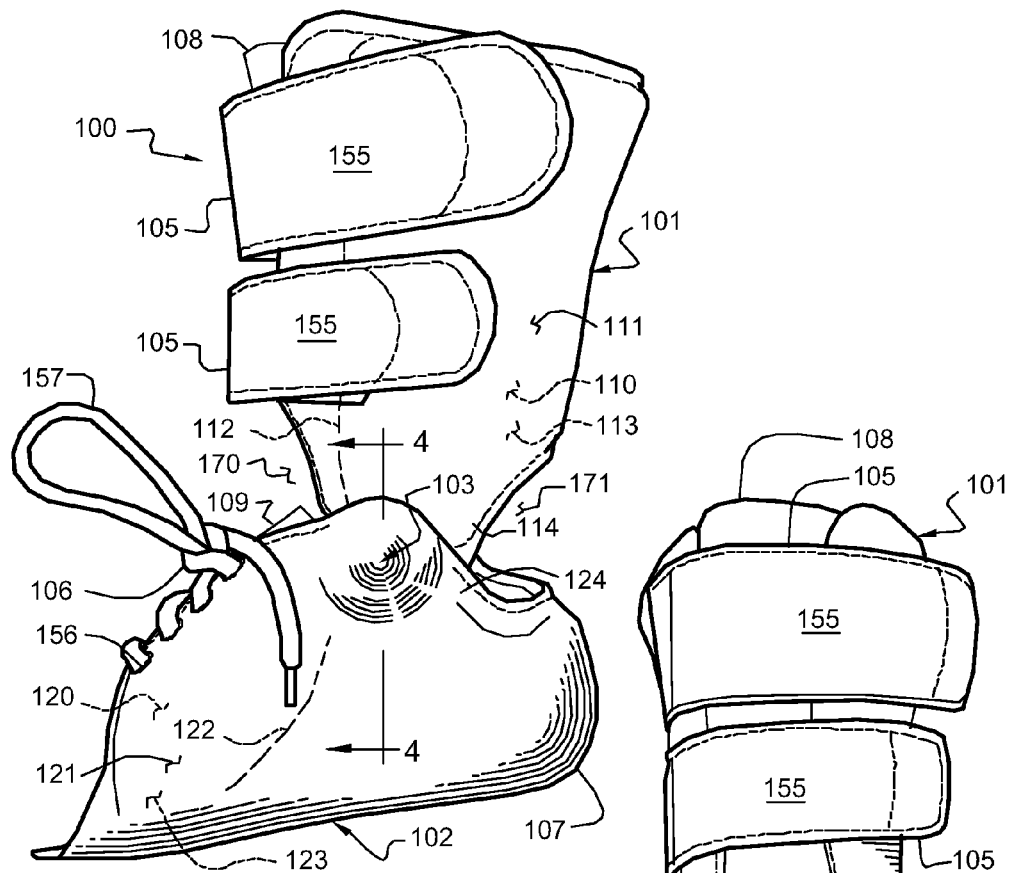
FIG. 1 is a side view of an articulated custom AFO system according to a preferred embodiment of the present invention.
Figure 2:
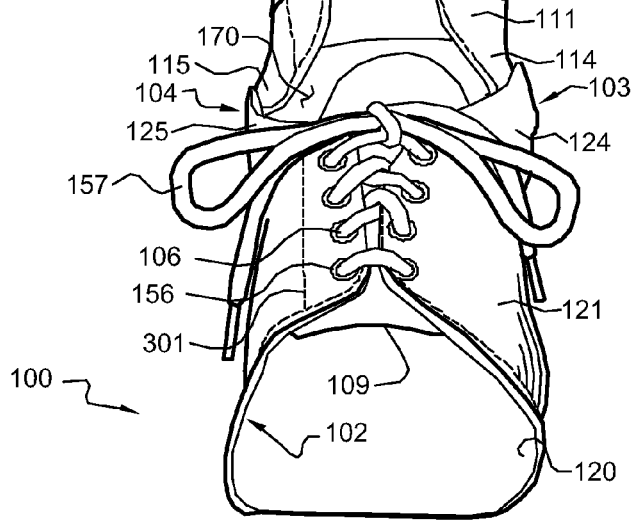
FIG. 2 is a front view of the articulated custom AFO system of FIG. 1.

FIG. 1 is a side view of an articulated custom Ankle-Foot Orthosis (AFO) system according to a preferred embodiment of the present invention. FIG. 2 is a front view of the articulated custom AFO system of FIG. 1. FIG. 3 is a rear view of the articulated custom AFO system of FIG. 1. FIG. 4 is a rear cross sectional view through the section 4-4 of FIG. 1.

With particular reference to FIGS. 1-4, articulated custom AFO 100 preferably has a calf section 101 hingedly connected to foot section 102 by hinges 103 and 104, as shown. Adjustably-tightenable calf tightener 105 and adjustably-tightenable foot tightener 106 preferably serve to adjustably tighten calf section 101 and foot section 102 to the calf and foot of the patient. Articulated brace 100 preferably has a heel 107, a calf tongue 108, and a foot tongue 109, as shown.

Inner calf lining 110 and outer calf lining 111 preferably enclose calf stiffener 112, as shown (see esp. FIG. 4). Calf padding 113 preferably lies at least between inner calf lining 110 and calf stiffener 112, as shown (see esp. FIG. 4). Inner foot lining 120 and outer foot lining 121 preferably enclose foot stiffener 122, as shown (see esp. FIG. 4). Foot padding 123 preferably lies at least between inner foot lining 120 and foot stiffener 122, as shown (see esp. FIG. 4).

FIG. 3 details how calf section 101 preferably substantially encircles at least a portion of the lower leg, with lateral calf hinge extension 114 and medial calf hinge extension 115 preferably extending down to form the inner surfaces of hinge 103 and hinge 104, respectively, as shown (this arrangement at least herein embodying wherein such at least one calf portion comprises at least one circumferential lower-leg support structured and arranged to circumferentially-support, by substantially encircling, the at least one lower leg of the at least one user, when worn). Foot section 102 preferably substantially encircles the heel and the midfoot, supporting the arch (this arrangement at least herein embodying wherein such at least one foot portion comprises arch support structured and arranged to provide support to arch of the foot of the at least one user, when worn; and this arrangement at least herein embodying wherein such at least one arch support comprises midfoot-and-heel-encircling support structured and arranged to substantially encircle midfoot and heel of the foot of the at least one user, providing support to the arch of the foot, when worn). Foot section 102 preferably does not extend to the toes portion of the foot. Lateral foot hinge extension 124 and medial foot hinge extension 125 preferably extend up to form the outer surfaces of hinges 103 and 104, respectively, as shown.

With reference to FIG. 2, calf tongue 108 and foot tongue 109 are preferably made from the same flexible material as the inner linings 110 and 120 and/or the outer linings 111 and 121, as shown. Preferably, tongues 108 and 109 cover the gaps in the front of articulated custom AFO 100, under tighteners 105 and 106, respectively, protecting the patient from chafing against tighteners 105 and 106. Tongues 108 and 109 preferably do not cover the area in front of the foot between calf section 101 and foot section 102, which comprises the front ankle opening 170 as shown, which is left open to facilitate the flexing of hinges 103 and 104 during walking. Similarly, a back ankle opening 171 is preferably provided as shown in FIG. 3 on the back area of the ankle between calf section 101 and foot section 102 to facilitate walking.

Inner linings 110 and 120, outer linings 111 and 121, calf tongue 108, and foot tongue 109 are preferably made of 2.5-oz, chromium-tanned cowhide leather, as shown. Leather has the advantages of being highly conformable and tolerable to the body of the patient. Leather is also durable, attractive, and is not damaged by brief contact with water. Upon reading the teachings of this specification, those with ordinary skill in the art will now understand that, under appropriate circumstances, considering such issues as available materials, user preference, advances in technology, etc., other soft, flexible materials substantially impervious to water damage, such as, for example, fabric, cotton, polyester, felt, nylon, vinyl, woven fabric, knitted fabric, nonwoven fabric, leather, neoprene, combinations of materials, laminates of materials, etc., may suffice for the inner linings, outer linings, and tongues.

Calf padding 113 and foot padding 123 are preferably fabricated from plastic foam, preferably thermoplastic foam, more preferably low-temperature thermoplastic foam, more preferably low-temperature thermoplastic foam comprising substantial malleability at about 180 degrees Fahrenheit. Most preferably, the thermoplastic foam comprises ¼-inch-thick PLASTIZOTE® sheet. Upon reading the teachings of this specification, those with ordinary skill in the art will now understand that, under appropriate circumstances, considering such issues as available materials, user preference, advances in technology, etc., other low temperature, thermally-formable foam materials, such as thermoplastic foam laminates, polyethylene foam, ethylene vinyl acetate foam, thermoplastic foam of other thicknesses, thermoplastic foam laminates, etc., may suffice.

Preferably, calf stiffener 112 and foot stiffener 122 are fabricated from plastic, preferably thermoplastic, more preferably low-temperature thermoplastic, more preferably low-temperature thermoplastic comprising substantial malleability at about 180 degrees Fahrenheit. Most preferably, calf stiffener 112 and foot stiffener 122 are fabricated from ORTHOPLAST® thermoplastic, manufactured by Johnson & Johnson of New Brunswick, N.J. Preferably, calf stiffener 112 and foot stiffener 122 are each fabricated from a sheet of one-eighth-inch-thick thermoplastic, as shown. Upon reading the teachings of this specification, those with ordinary skill in the art will now understand that, under appropriate circumstances, considering such issues as available materials, user preference, advances in technology, etc., other low temperature thermally formable materials, such as MULTIFORM PLASTIC™, X-LITE PLUS™, EZEFORM SPLINTING MATERIAL™, MULTIFORM CLEAR™, polyethylene, thermoplastic laminates, etc., may suffice.

FIG. 2 is a front view of the articulated custom AFO system of FIG. 1. In this embodiment, adjustably-tightenable calf tightener 105 preferably comprises two leather-covered hook and loop straps 155, as shown. In this embodiment, adjustably-tightenable foot tightener 106 preferably comprises a plurality of grommets 156 with a lace 157, as shown. Preferably, adjustably-tightenable calf tightener 105 and adjustably-tightenable foot tightener 106 each comprise either hook and loop fasteners or grommets and laces. Upon reading the teachings of this specification, those with ordinary skill in the art will now understand that, under appropriate circumstances, considering such issues as user preference, available materials, advances in technology, etc., other methods of adjustably closing articulated custom AFO 100, such as elastic tighteners, cinched straps, zippers, etc., may suffice.

FIG. 3 is a rear view of the articulated custom AFO system of FIG. 1. The overlapping structure of hinges 103 and 104 is shown. Under appropriate circumstances, medial calf hinge extension 115 and lateral calf hinge extension 114 may form the outside surfaces of joints 104 and 103, and foot extensions 125 and 124 may form the inside surfaces of joints 104 and 103.

FIG. 4 is a cross sectional view of section 4-4 of FIG. 1. This view details the layering of the linings, paddings, and stiffeners. Outer calf lining 111, calf stiffener 112, calf padding 113, and inner calf lining 110 are shown. Outer foot lining 121, foot stiffener 122, foot padding 123, and inner foot lining 120 are also shown.

Hinge 103 preferably comprises the overlapping areas of lateral calf hinge extension 114 and lateral foot hinge extension 124, and also comprises hinge 191, as shown. Hinge 104 preferably comprises the overlapping areas of medial calf hinge extension 115 and medial foot hinge extension 125, and also comprises hinge 192, as shown in FIG. 3. Preferably, hinges 191 and 192 are pin or rivet hinges known to those of skill in the art, as shown.

Preferably, lateral calf hinge extension 114 and lateral foot hinge extension 124, and/or medial calf hinge extension 115 and medial foot hinge extension 125, may not overlap, and may instead support another type of hinge, such as, for example, standard action articulated custom AFO hinges manufactured or sold by Becker Orthopedic of Troy, Mich., USA. Upon reading the teachings of this specification, those with ordinary skill in the art will now understand that, under appropriate circumstances, considering such issues as patient needs, advances in technology, availability of materials, desired strength of the hinge, etc., other hinges and/or joints, such as cambered hinges, hinges with stops, hinges with dorsiflexion assist, locking joints, multiple-center joints, resilient joints, etc., may suffice.

The attachment means, comprising attachers, are preferably structured to attach the various parts of articulated custom AFO 100 to each other. Attachers may comprise stitches 301, glue 302, heat bonding inherent in the thermoshaping process, or other appropriate means for joining pliable materials together. For example, glue 302 preferably joins the inner linings 110 and 120 and outer linings 111 and 121 to each other, and joins stiffeners 112 and 122 are attached to pads 113 and 123, and joins the pads 113 and 123 to the inner linings 110 and 120, and joins the outer linings 111 and 121 to the stiffeners 112 and 122, pads 113 and 123, and inner linings 110 and 120. Glue 302 is preferably a thin adhesive layer that preferably adheres all adjacent stiffener-padding, lining-padding, lining-stiffener, and lining-lining interfaces.

Most preferably, glue 302 comprises rubber cement. FIG. 4 shows the layers of articulated custom AFO 100 attached together with glue 302 at all of the above-specified interfaces.

Also, attachers, preferably stitches 301, preferably join the tongues 108 and 109 and tighteners 105 and 106 to the calf and foot sections 101 and 102, respectively, as shown in FIG. 2. Furthermore, attachers, preferably stitches 301, join the back seams of the inner linings 110 and 120 and outer linings 111 and 121, and the perimeters of the inner linings 110 and 120 and outer linings 111 and 121, as shown in FIG. 3. Upon reading the teachings of this specification, those with ordinary skill in the art will now understand that, under appropriate circumstances, considering such issues as materials requirements, user preference, advances in technology, etc., other attachment means, such as natural adhesion of the stiffener and padding when hot, melt or ultrasonic welding, edge binding, etc., may suffice.

Articulated custom AFO 100 is preferably manufactured using a custom plaster cast 130 of the wearer's foot and leg. A preferred manufacturing procedure is disclosed below.

FIG. 5 illustrates a cotton stockinette 145 placed on the foot of a patient. The cotton stockinette 145 preferably protects the leg of the patient from the plaster casting process, and also provides a suitable marking surface for transferable diagnostic markings 500.

FIG. 6A shows various preferred transferable diagnostic markings 500 placed on stockinette 145. Transferable diagnostic markings 500 preferably transfer to the positive cast 130 (as shown esp. in FIG. 14) and map the exact locations and types of therapeutic modifications to be made to the final positive cast 130. For example, building up the positive cast 130 will result in extra space in the final articulated custom AFO 100 in order to, for example, avoid placing pressure on a sensitive area. Grinding down the positive cast 130 will result in less space in the final articulated custom AFO 100 in order to, for example, build up arch support. For articulated custom AFOs 100 of the current invention, the location and axis of the ankle's plantar/dorsal motion is preferably marked and built up to provide the proper location, shape, and space for hinges 103 and 104, according to the skill and experience of the brace maker, as shown esp. in FIG. 22C.

FIG. 6B illustrates a preferred diagnostic marking 500. This particular diagnostic marking 500 is used to indicate a bony prominence that will result in a 5 mm (millimeter) build-up on the positive mold plaster casting 130, which will be described in greater detail below. This mark is preferably a solid circle 138 around an X 126 as shown; the X 126 marks the apex of the bony prominence. The diameter of the solid circle 138 is determined by the experience and skill of the brace-maker and preferably indicates the area of plaster build up desired on the positive cast 130.

FIG. 6C illustrates a preferred diagnostic marking 500. FIG. 6C shows a diagnostic marking 500 used to indicate an extreme bony prominence, which will result in a 10 mm (1 centimeter) plaster build-up on the positive cast 130. This mark is preferably a solid circle 138 around multiple crossing "x" 126 marks on the extreme bony prominence apex, as shown. The diameter of the solid circle 138 is determined by the experience and skill of the brace-maker and preferably indicates the area of plaster build-up desired on the positive cast 130.

FIG. 6D illustrates a preferred diagnostic marking 500. FIG. 6D shows a diagnostic marking 500 preferably used to indicate bone that is not prominent but will need a small plaster build-up for additional support, typically 1.5 mm-3 mm on the positive cast 130. This mark is preferably a solid circle 138 around the bone with two parallel lines 132 along the bone, as shown.

FIG. 6E illustrates a preferred diagnostic marking 500. FIG. 6E shows a diagnostic marking 500 used to indicate painful or sensitive tissue, including scar tissue. Preferably, an oblong circle 144, as shown, is drawn around the sensitive or painful tissue that will result in a 5 mm-10 mm plaster build-up on the positive cast 130. The plaster build-up will allow room for the use of added padding in the painful areas. FIG. 6E also shows scar tissue as marked with a longer straight line 134 and several small shorter lines crossing perpendicular to the longer straight line 134.

Figure 6F:
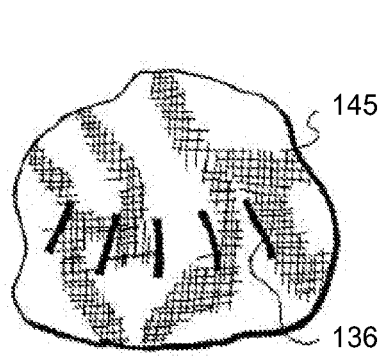
FIG. 6F illustrates preferred diagnostic indicia.

FIG. 6F illustrates a preferred diagnostic marking 500. FIG. 6F shows a diagnostic marking 500 preferably used to indicate where extra support is needed or wanted as determined by the experience and skill of the brace-maker and indicates the area of plaster build-up that will be added to the positive cast 130. Shown here as an embodiment is the diagnostic marking 500 used to indicate a flat arch with a needed extra support that will require cutting out of the positive cast 130 in the medial arch and anterior sastitacacum area of the foot. This mark is preferably indicated by several lines 136 parallel to each other along the area of support as shown, the amount to be cut out being directly correlated with the closeness of the markings.

Figure 7:
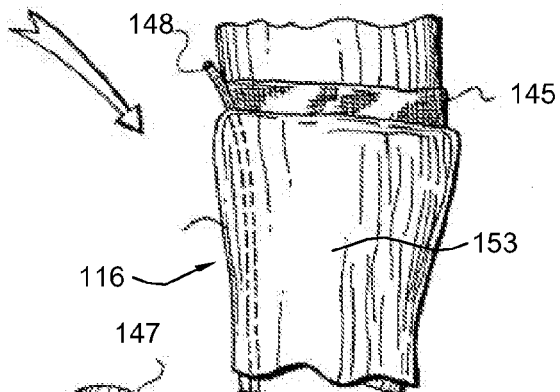
FIG. 7 shows the process of making a negative cast of the patient's foot.
Figure 8:
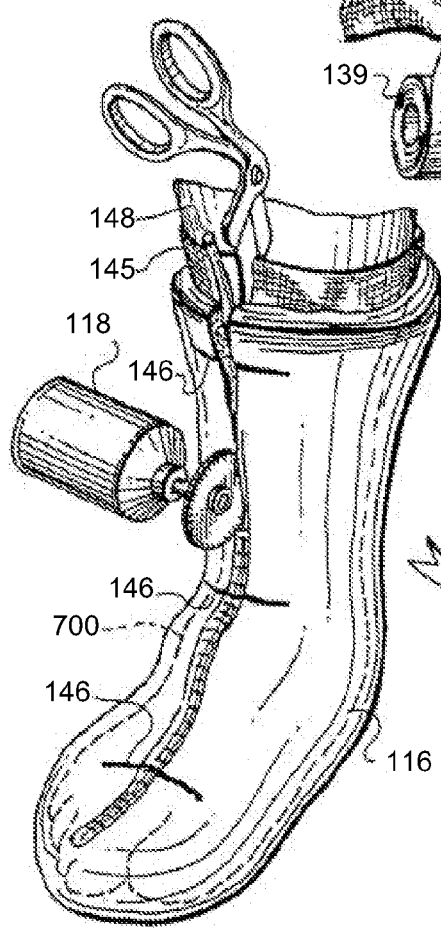
FIG. 8 shows the removal of a finished negative cast from the patient's foot.

FIG. 7 shows the process of making a negative cast 116 of the patient's foot. With the castmaker making sure that the patient's sole is steady in a horizontal plane and that the patient's lower leg is placed vertically, elastic plaster bandages 139 are preferably wrapped around the cotton stockinette 145 in a manner consistent with the experience and skill of the brace-maker, preferably followed by a more solid plaster bandage 147, as shown. The solid plaster bandage 147 is preferably wrapped around the elastic plaster bandage 139 wrap and both wraps preferably cover a small diameter surgical tubing 148 which is preferably used and placed as shown in FIG. 8 along the centerline of the top of the foot 700. This surgical tubing 148 will be used to facilitate removal of the negative cast 116 as shown in FIG. 8. Optionally, wet plaster 153 is placed over solid plaster bandage 147. The preferred wet plaster 153 used for this process is standard in the medical industry and known as quick dry medical cast plaster.

FIG. 8 shows the removal of a finished negative cast 116 from the patient's foot. The negative cast 116 is preferably cut off with a plaster cast cutting tool 118 as shown, usually a rotary saw of a type well-known by a person skilled in the art. As shown, the cut is preferably made along the surgical tubing 148 previously implanted during the elastic plaster bandage 139 wrap sequence. Before the cut is made, to assist in realigning of the cut line of the negative cast 116 before it used to make a positive cast, alignment marks 146 across the cut line are preferably made as shown. The negative cast 116 is then removed from the patient's foot 700.

Figure 9:
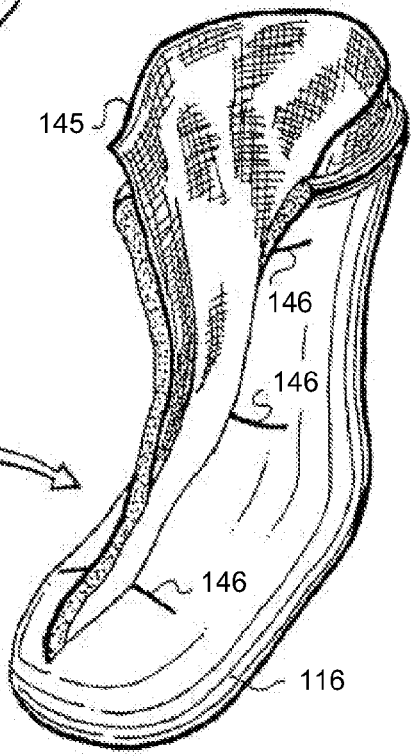
FIG. 9 shows the completed negative cast of the patient's foot.

FIG. 9 shows the completed negative cast 116 of the patient's foot with the patient's foot removed.

Figures 14, 15, 16, 17:
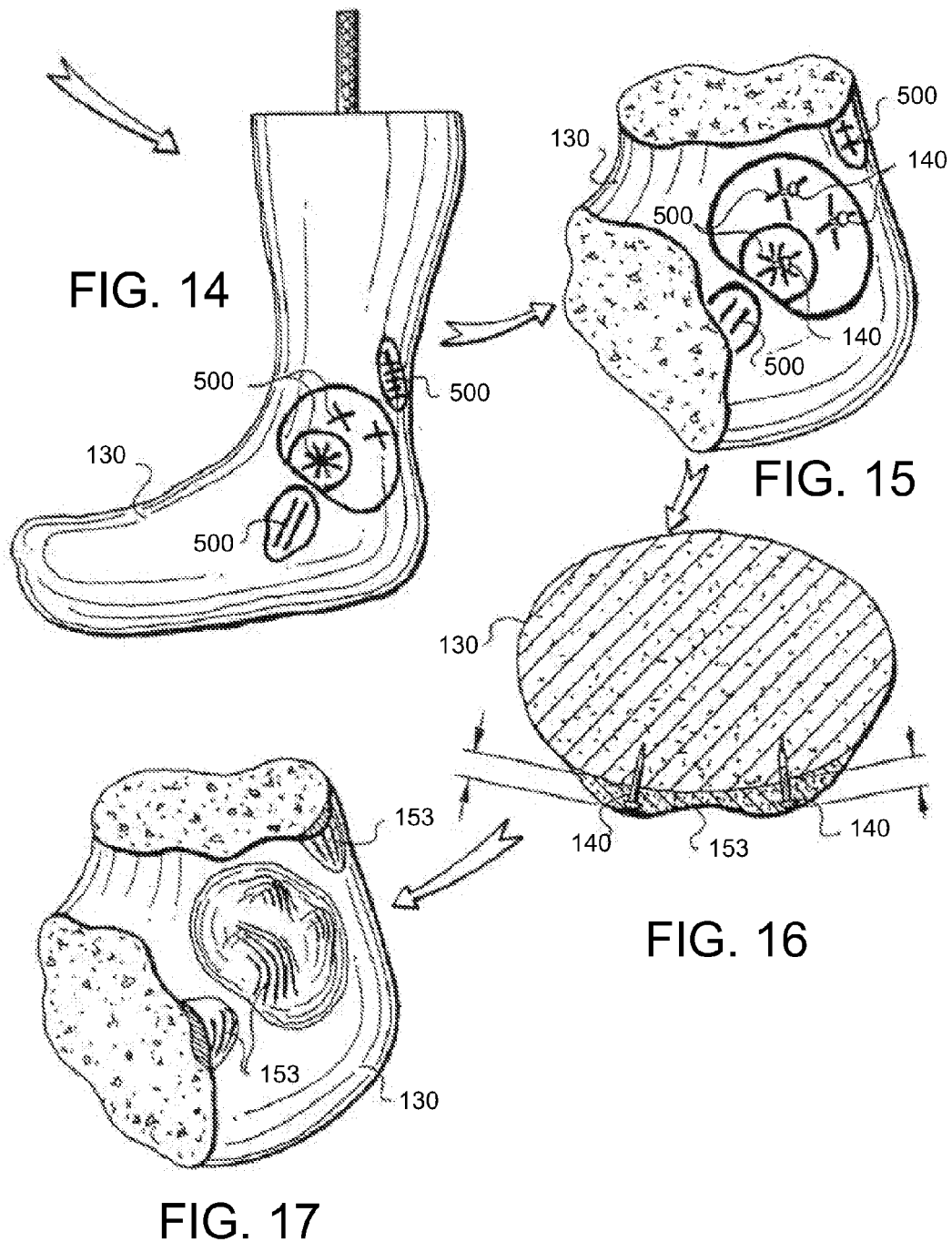
FIG. 14 shows the finished positive cast with transferred diagnostic indicia.
FIG. 15 shows the placement of depth markers on the diagnostic indicia.
FIG. 16 shows a cross sectional view of the placement of depth markers in the diagnostic indicia.
FIG. 17 shows plaster smoothly built up to the level of the depth markers.

FIG. 10 shows the stockinette 145 being removed from the negative cast 116. The cotton stockinette 145 preferably is carefully removed and peeled away from the negative cast 116, as shown. When done correctly, the previous diagnostic markings 500, described above and preferably of the types shown in FIG. 6B through FIG. 6F, will have transferred to the inside of the negative cast 116 as shown in FIG. 14.

FIG. 11 shows the negative cast 116 being sealed prior to making a positive cast 130. The reassembly of the negative cast 116 is performed in the usual and well-known manner.

The two sides, partially separated during removal from the patient's foot 700, are preferably reassembled by gently urging the cut ends together, making sure the previously marked alignment marks 146 are in alignment, as shown.

FIG. 12 shows filling the negative cast 116 with plaster 153 and a rebar 154. The inside of the negative cast 116 is preferably coated with a releasing agent, typically a soap solution of a kind well known to those in the art. A 3/8" steel rebar rod 154 is preferably placed in the center of the negative cast 116 as wet plaster 153 is poured into the negative cast 116, as shown. The wet plaster 153 preferably used for this process is standard in the medical industry and known as quick dry medical cast plaster. This 3/8 steel rebar rod 154 is preferably used to hold the positive cast 130 during various phases in the articulated custom AFO 100 manufacturing process.

FIG. 13 shows removing the negative cast 116 from the positive cast 130. After the wet plaster 153 has set, the negative cast 116 is cut off with a plaster cutting tool 118, as shown. The cut is preferably made along the surgical tubing 148 previously implanted during the elastic plaster bandage 139 wrap sequence and still attached to the negative cast 116. The diagnostic markings 500 will have preferably transferred to the exterior of the positive cast 130, creating a replica of the patient's foot with the brace-maker's markings 500 as shown esp. in FIG. 14.

FIG. 14 shows the finished positive cast 130 with transferred preferred diagnostic indicia 500.

FIG. 15 shows the placement of depth markers on the diagnostic marking 500. Specifically illustrated in FIG. 15 is the working of the positive cast 130 by preferably adding small nails 140 where plaster build-up is indicated by the diagnostic markings 500, as shown. These small nails 140 are preferably inserted into the positive cast 130 until the spacing between the top of the small nail 140 head and the positive cast 130 is equal to the amount of plaster build-up (5 millimeter, 10 millimeter, etc.) that will be needed as indicated by the diagnostic markings 500 previously applied, as shown.

FIG. 16 shows a cross sectional view of the placement of small nails 140 as depth markers in the diagnostic markings 500. Additional wet plaster 153 is preferably applied until it is even with the small nail 140 heads and in conjunction with the areas that will need extra support as determined by the skill of the brace-maker, as shown (at least embodying herein making at least one build-up of such at least one positive cast).

FIG. 17 shows plaster smoothly built up to the level of the depth marker nails 140. At this point in manufacturing, an essentially flat, essentially circular platform about one to two inches in diameter, approximately perpendicular to the axis of plantar/dorsal motion, is preferably smoothly built up with plaster 153 on each lateral hinge 103 and medial hinge 104 placement point in order to shape the hinges 103 and 104 and slightly offset the hinges 103 and 104 away from the foot, as shown in FIG. 22C (at least embodying herein making at least one build-up of such at least one positive cast to provide for the placement of at least one medial hinge and at least one lateral hinge). The proper location of the hinges 103 and 104 on the positive cast 130 is preferably indicated by diagnostic indicia 500 or may be determined by the skill of the brace maker. After the added wet plaster 153 has set the brace-maker will preferably begin the process of sanding the positive cast 130 smooth until it is the correct shape as determined by the experience and skill of the brace-maker.

Figure 18:
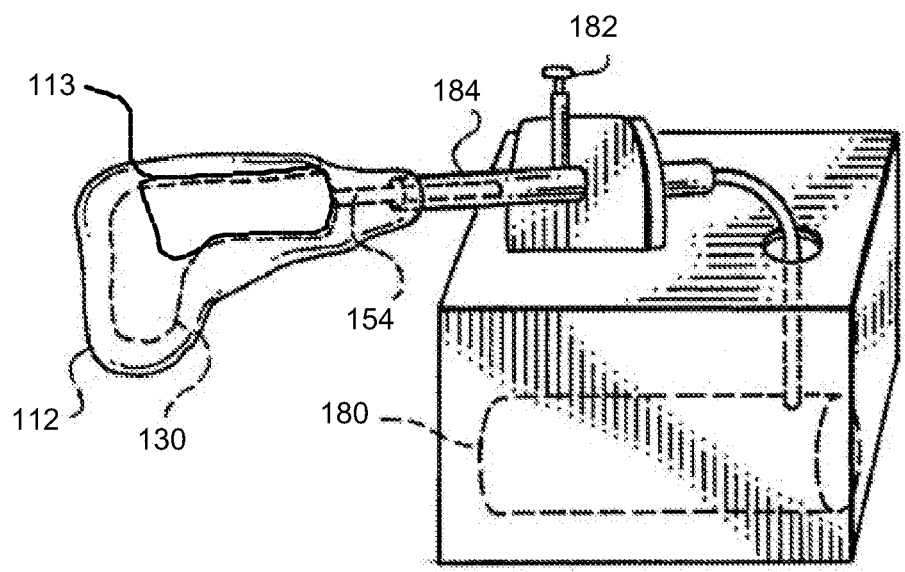
FIG. 18 shows the process of vacuum thermoforming first sheets of thermoformable plastic and foam to the positive cast.

FIG. 18 shows the process of vacuum thermoforming first sheets of thermoformable plastic and foam to the positive cast 130 to form the calf stiffener 112 and calf padding 113. Illustrated in FIG. 18 is the vacuum fitting process specifically showing a vacuum fitting means preferably embodied by a vacuum pump and motor 180, a valve 182, and a suction inlet pipe 184, as shown. In applicant's preferred embodiment, a 1/4 horsepower motor is used to run the vacuum pump.

Prior to attachment of the positive cast 130 to the vacuum fitting means, the positive cast 130 is preferably fitted with a talcum-powdered nylon material or stocking which is used to prevent the heated calf padding 113 from adhering to the positive cast 130. The attachment of the positive cast 130 to the vacuum fitting means is preferably accomplished by sliding the 3/8 inch steel rebar rod 154, extending from the upper end of the positive cast 130, into the end opening of the suction inlet pipe 184, as shown.

The calf stiffener 112 and calf padding 113 (in the form of flat sheets of thermoplastic material) are preferably softened by being heated in an oven to a temperature of approximately 400 degrees Fahrenheit for approximately 3 minutes. The heated calf padding 113 is then removed from the oven while wearing appropriate gloves and preferably placed at least around the calf and hinge areas of positive cast 130, as shown. The heated calf stiffener 112 is then removed from the oven while wearing appropriate gloves and preferably placed around the entire positive cast 130, as shown. The free ends of the calf stiffener 112 are preferably touched together and touched to the suction inlet pipe 184 (near its end opening) thereby forming an air-tight shroud around the positive cast 130, as shown.

The negative pressure is preferably maintained until calf stiffener 112 cools to a temperature that will allow handling of the stiffener element without altering its physical shape, usually about one minute.

Figure 19:
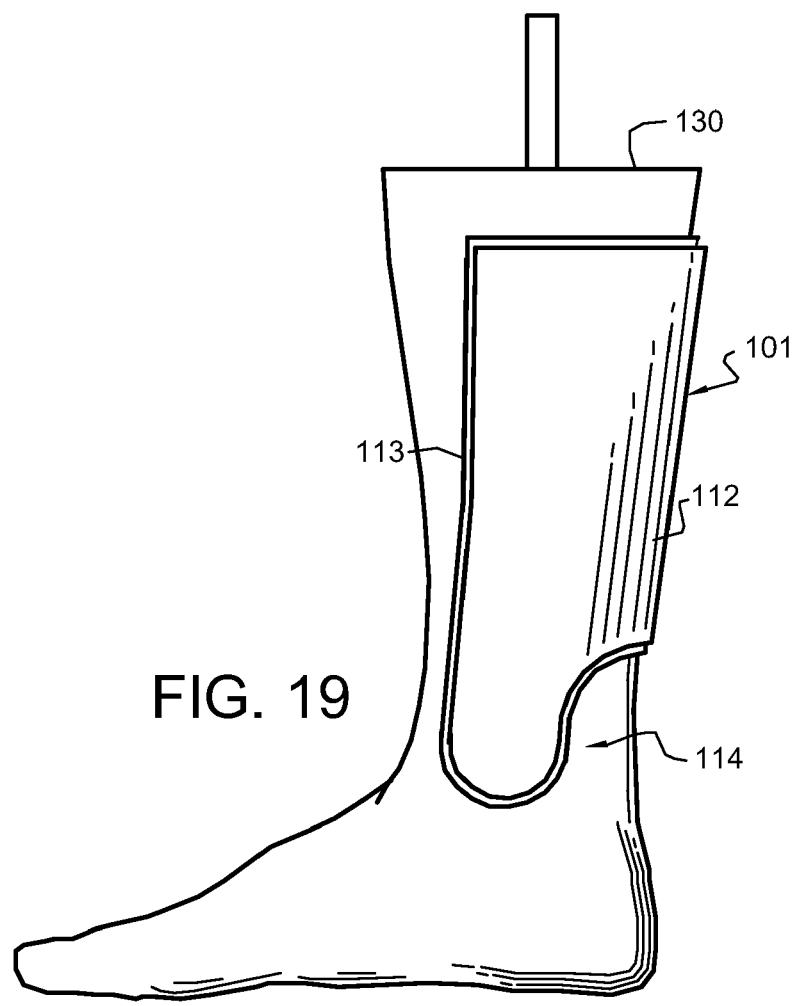
FIG. 19 shows the trimmed calf section of the articulated custom AFO on the positive cast.

FIG. 19 shows the finished trimmed calf section 101 of the articulated custom AFO 100 on the positive cast 130. First, the positive cast 130 encased in calf stiffener 112 is preferably removed from the vacuum fitting means (shown in FIG. 18) and calf stiffener 112 is preferably marked along a trim line wherein such trim line is located by the brace maker according to the amount and type of support required by the individual patient (preferably as previously indicated by the markings 500 on the positive cast 130) in the approximate shape shown in FIG. 19. Lateral calf hinge extension 114 and medial calf hinge extension 115 preferably extend down to form the inner surfaces of hinge 103 and hinge 104, respectively, as shown. Calf stiffener 112 is then removed from the positive cast 130, and is preferably trimmed along the trim lines (at least embodying herein using such at least one positive cast, making at least one calf stiffener for use within such at least one material layers in making such at least one ankle-foot orthosis for such patient). Calf padding 113 is preferably also removed from the positive cast 130 and trimmed at this point. Preferably, calf padding 113 may extend beyond the perimeter of trimmed calf stiffener 112, as shown.

FIG. 20 shows the process of vacuum thermoforming second sheets of thermoformable plastic and foam over the positive cast and the trimmed calf stiffener 112 and calf padding 113. The trimmed calf stiffener 112 with calf padding 113 is preferably first put back on the positive cast 130 in the proper position (as shown in FIG. 19), and another layer of thermoformable foam, and then plastic, is preferably vacuum formed over calf stiffener 112 and calf padding 113 and the positive cast 130, as shown. In this case, foot padding 123 is preferably placed to cover at least the foot, hinge, and heel portions of positive cast 130 as shown, and then foot stiffener 122 is placed to cover the entire positive cast 130, the foot padding 123, the trimmed calf stiffener 112 and padding 113, and the free edges of foot stiffener 122 are touched together to form a vacuum seal, as shown. The negative pressure is preferably maintained until foot stiffener 122 cools to a temperature that will allow physical handling of the stiffener element without altering its physical shape, usually about one minute.

Next, the positive cast 130 encased in foot stiffener 122 is preferably removed from the vacuum fitting means. Then, foot padding 123 and foot stiffener 122 are preferably marked along a trim line wherein such trim line is located by the brace maker according to the amount and type of support required by the individual patient (as previously indicated by the markings 500 on the positive cast 130), and also to overlap calf stiffener 112 at the hinge-forming lateral and medial extensions 114 and 115.

The foot stiffener 122 is then removed from the positive cast 130, and is preferably trimmed along the trim lines, as shown esp. in FIG. 22C (at least embodying herein using such at least one positive cast, making at least one foot stiffener for use within such at least one material layers in making such at least one ankle-foot orthosis for such patient). Foot padding 123 is also preferably trimmed at this point, along a trim line wherein such trim line is located by the brace maker according to the amount and type of support required by the individual patient (as previously indicated by the markings 103 on the positive cast 130), as shown in FIG. 22C. Foot padding 123 may preferably extend beyond the perimeter of trimmed foot stiffener 122, as shown in FIG. 22C.

Preferably, all of the stiffeners and paddings may be beveled or tapered at the edges, to provide greater comfort to the patient. Preferably, all of the linings are skived (shaved thin) at the edges and seams to provide greater comfort for the patient.

FIG. 21A shows the leather lining pieces 110 and 111 for the calf section 101 which are preferably cut out according to a paper pattern (at least embodying herein making at least one support brace pattern from such at least one positive cast; and also embodying herein making at least one material layers to fit such at least one support brace pattern). The inner lining pieces 110 for the calf section 101 are attached, preferably sewn, together along back seam 173, as shown. The outer lining pieces 111 for the calf section 101 are attached, preferably sewn, together along back seam 174, as shown. Upon reading the teachings of this specification, those with ordinary skill in the art will now understand that, under appropriate circumstances, considering such issues as advances in technology, user preference, etc., other arrangements, such as stretching the linings to shape, improvising a pattern, gluing the seams, using one piece of material without seams, etc., may suffice.

FIG. 21B shows the completed inner calf lining 110 and outer calf lining 111.

FIG. 21C shows the calf leather lining pieces 110 and 111 glued and sewn to the calf section 101 (at least embodying herein at least one calf portion, having inside and outside surfaces, of such articulated custom AFO system). Inner calf lining 110 is preferably first placed back onto positive cast 130 in the correct position, and calf pad 113 is attached, preferably glued, in the correct position over inner calf lining 110. Calf stiffener 112 (at least embodying herein calf stiffener means, having medial and lateral sides and inside and outside surfaces, for stiffly supporting such the at least one calf portion) is then attached, preferably glued, in the correct position onto calf pad 113. Outer calf lining 111 (at least embodying herein calf outer lining means for pliably lining at least such the outside surface of such calf stiffener means) is then attached, preferably glued, in the correct position onto calf stiffener 112, calf padding 113 (at least embodying herein calf padding means for padding at least substantially such inner surface of such calf stiffener means), and inner calf lining 110 (at least embodying herein calf inner lining means for pliably lining at least such inside surface of such at least one calf portion), as shown (at least embodying herein attachment means for attaching such calf stiffener means with such calf outer lining means). Next, calf section 101 is preferably trimmed, and is preferably sewn around selected parts of the perimeter for reinforcement (at least embodying herein trimming and finishing such at least one articulated custom AFO system), as shown in FIG. 23.

FIG. 22A shows the leather lining pieces 120 and 121 for the foot section 102, which may be cut out according to a paper pattern. The inner foot lining 120 is attached, preferably sewn, together along back seam 175 to form a hollow for the heel, as shown in FIG. 22B. The outer foot lining 121 is attached, preferably sewn, together along back seam 176 to form a hollow for the heel, as shown in FIG. 22B. Upon reading the teachings of this specification, those with ordinary skill in the art will now understand that, under appropriate circumstances, considering such issues as advances in technology, user preference, etc., other arrangements, such as stretching the linings to shape, improvising a pattern, gluing the seams, using one piece of material without seams, etc., may suffice.

FIG. 22B shows the completed inner foot lining 120 and outer foot lining 121.

FIG. 22C shows the leather lining pieces 120 and 121 glued and sewn to foot stiffener 122 (at least embodying herein attaching such at least one material layers to such at least one calf stiffener and at least one foot stiffener) and foot pad 123 to form the foot section 102 (at least embodying herein at least one foot portion, having inside and outside surfaces, of such articulated custom AFO system). Inner foot lining 120 is first preferably placed onto positive cast 130 in the correct position, and foot pad 123 is attached, preferably glued, over inner foot lining 120. Foot stiffener 122 (at least embodying herein foot stiffener means, having medial and lateral sides and inside and outside surfaces, for stiffly supporting such at least one foot portion) is then attached, preferably glued, onto foot pad 123. Outer foot lining 121 (at least embodying herein foot outer lining means for pliably lining at least the outside surface of such foot stiffener means) is then attached, preferably glued, onto foot stiffener 122, foot pad 123 (at least embodying herein foot padding means for padding at least substantially such inner surface of such foot stiffener means), and inner foot lining 120 (at least embodying herein foot inner lining means for pliably lining at least such inside surface of such at least one foot portion), as shown (at least embodying herein attachment means for attaching such foot stiffener means with such foot outer lining means). Next, foot section 102 is preferably trimmed, and is preferably sewn around selected parts of the perimeter for reinforcement, as shown.

FIG. 23 shows the calf section 101 with calf tongue 108 (at least embodying herein calf tongue means for covering the area at least under such calf tightener means) and adjustably tightenable calf tightener 105 (at least embodying herein calf tightener means for tightening such calf outer lining means about the calf of the at least one user) attached. Calf tongue 108 is preferably attached, more preferably sewn, inside the front of calf section 101, as shown (at least embodying herein attaching at least one tongue). Adjustably tightenable calf tightener 105 (at least embodying herein attachment means for attaching such tightener means with such calf outer lining means), is preferably attached, more preferably sewn, to the front of calf section 101, as shown (at least embodying herein attaching at least one tightener).

FIG. 24 shows the foot section 102 with foot tongue 109 (at least embodying herein foot tongue means for covering the area at least under such foot tightener means) and adjustably tightenable foot tightener 106 (at least embodying herein foot tightener means for tightening such foot outer lining means about the foot of the at least one user) attached. Foot tongue 109 is preferably attached, more preferably sewn, inside the front of foot section 102, as shown. Adjustably tightenable foot tightener 106 is preferably attached, more preferably riveted, to the front of foot section 102, as shown.

Figure 25A:
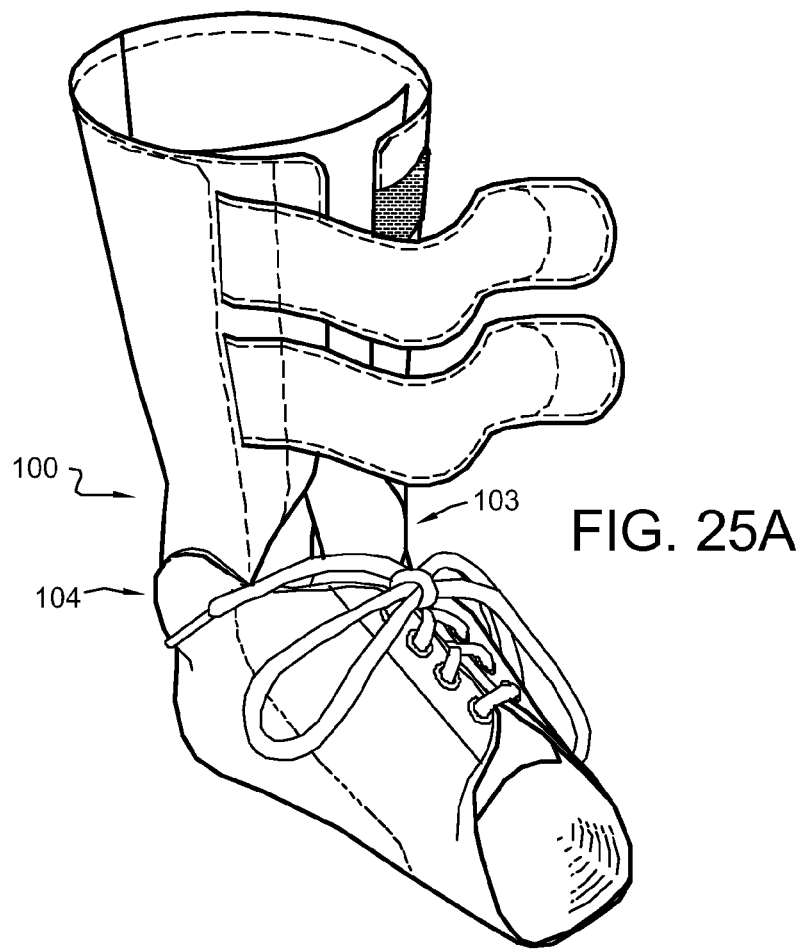
FIG. 25A shows the completed articulated custom AFO system with the hinges installed.

FIG. 25A shows the completed preferred articulated custom AFO 100 with medial hinge 104 (at least embodying herein medial hinge means for hingedly connecting such medial side of such calf stiffener means to such medial side of such foot stiffener means) and lateral hinge 103 (at least embodying herein lateral hinge means for hingedly connecting such lateral side of such calf stiffener means to such lateral side of such foot stiffener means) installed.

Figure 25B:
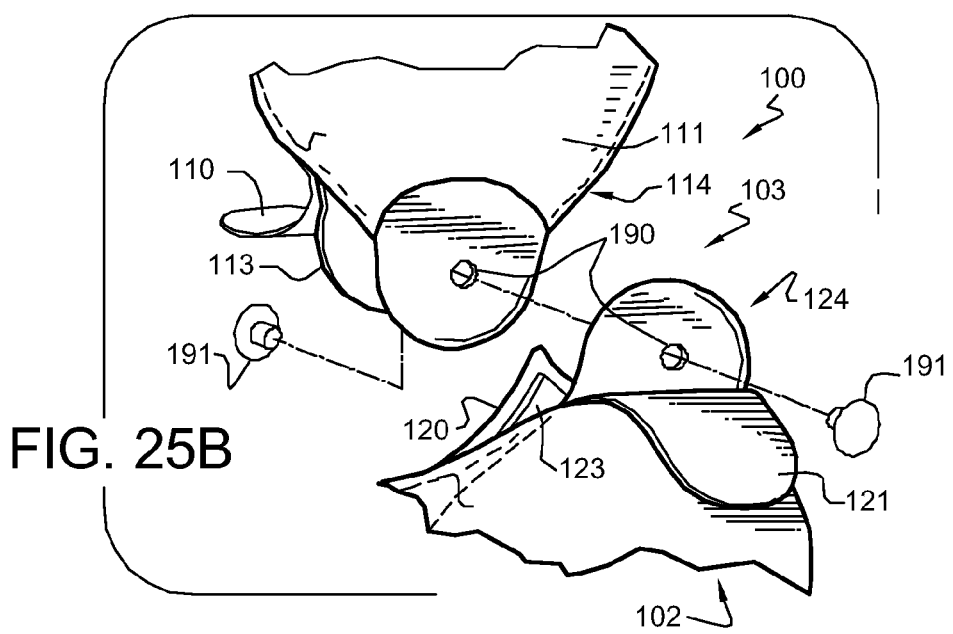
FIG. 25B shows the construction of a preferred rivet hinge.

FIG. 25B details the construction of lateral hinge 103, which is preferably installed by the steps of:

1) un-attaching all paddings and linings from lateral calf hinge extension 114 and lateral foot hinge extension 124;
2) aligning lateral calf hinge extension 114 and lateral foot hinge extension 124, with lateral foot hinge extension 124 outside of lateral calf hinge extension 114;
3) trimming foot padding 123 and inner foot lining 120 away from the overlapping hinge area of lateral foot extension 124;
4) trimming outer calf lining 111 away from the overlapping hinge area of lateral calf hinge extension 114;
5) drilling hole 190 through lateral calf hinge extension 114 and lateral foot hinge extension 124 at the correct place for hinge 103;
6) installing hinge 191 through hole 190 (at least embodying herein attaching such at least one medial hinge to such at least one calf stiffener and such at least one foot stiffener);
7) reattaching calf padding 113 and inner calf lining 110 to lateral calf hinge extension 114;
8) reattaching outer foot lining 121 to lateral foot hinge extension 124 (at least embodying herein wherein such foot outer lining means substantially covers the outer surface of such lateral hinge means); and
9) trimming calf padding 113, inner calf lining 110, and outer foot lining 121 to conform to the perimeter of lateral hinge 103, as shown (at least embodying herein a method of making at least one custom articulated custom AFO system, for permitting dorsal and plantar ankle flexion between a calf and a foot of a lower leg of at least one user, comprising the steps of: making at least one custom articulated AFO; making at least one outer calf lining; making at least one outer foot lining; attaching such at least one calf outer lining to such at least one custom articulated AFO; and attaching such at least one foot outer lining to such at least one custom articulated AFO).

Medial hinge 104 is preferably installed in a similar fashion on the medial side of articulated custom AFO 100 (at least embodying herein wherein such foot outer lining means substantially covers the outer surface of such lateral hinge means). Upon reading the teachings of this specification, those with ordinary skill in the art will now understand that, under appropriate circumstances, considering such issues as advances in technology, user preference, patient needs, etc., other steps, such as not trimming the linings and paddings away from the interior of the hinge, not covering the exterior of the hinge, etc., may suffice.

Figure 26A:
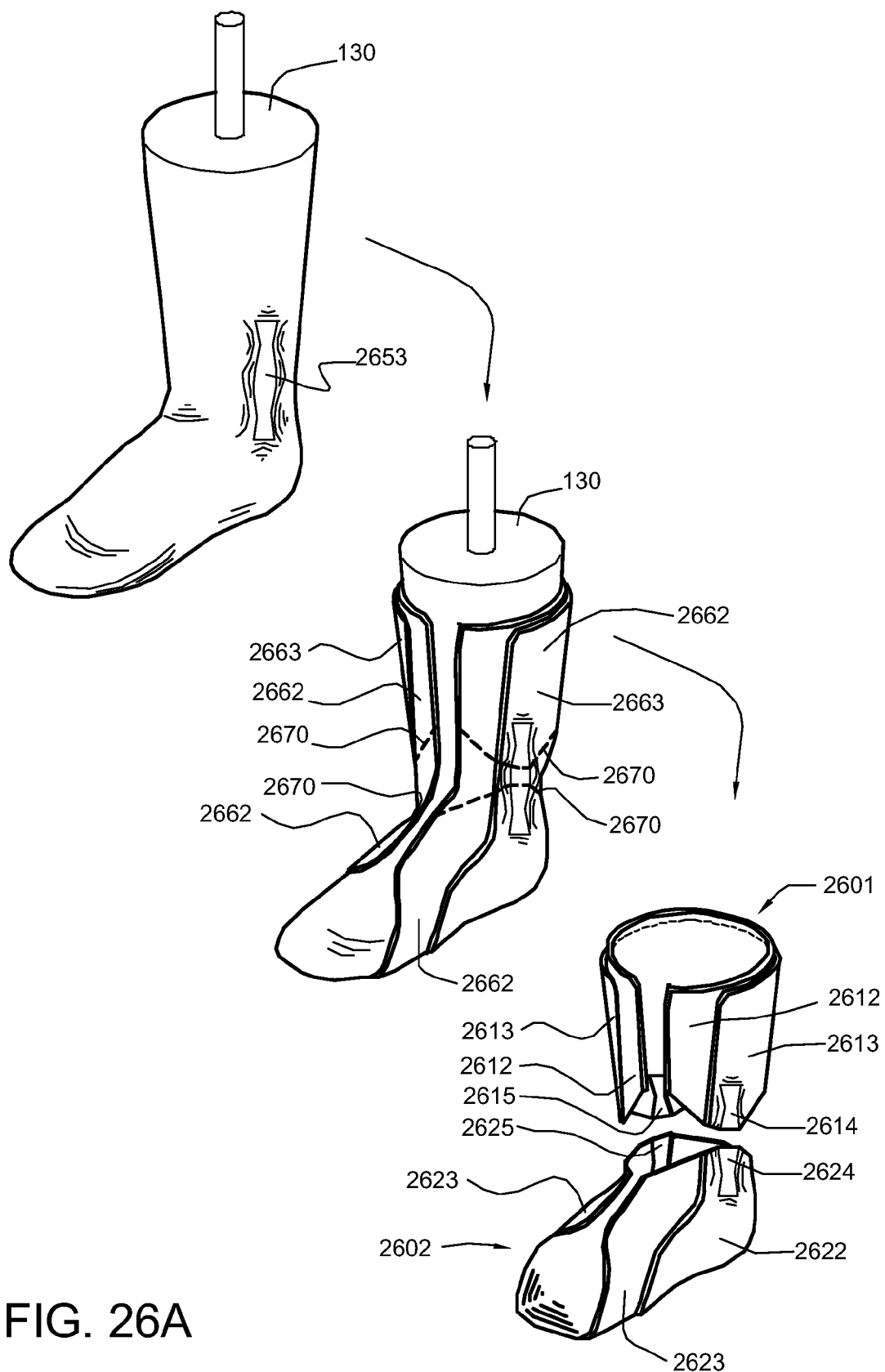
FIG. 26A shows steps in a process of manufacturing an articulated custom AFO system according to a preferred embodiment of the present invention

FIG. 26A shows steps in a process of manufacturing an articulated custom AFO 2600 according to a preferred embodiment of the present invention. Preferably, articulated custom AFO 2600 utilizes premade ankle hinges 2603, such as, for example, Gaffney ankle hinge model number P/N 710, manufactured by Gaffney Technology of Hillsboro, Oreg., USA, as shown especially in FIG. 26B. Articulated custom AFO 2600 is preferably manufactured in one piece by molding brace stiffener 2663 and brace padding 2662 onto built-up cast 130, and then cutting brace stiffener 2663 and brace padding 2662 into a calf section 2601 and a foot section 2602, and then installing premade ankle hinges 2603 to hingedly connect calf section 2601 and foot section 2602.

First, cast 130 is preferably built up on the medial and lateral sides by a skilled brace-maker to create a buildup 2653 which will create recessed spaces 2614 and 2615 in calf section 2601 and recessed spaces 2624 and 2625 in foot section 2602 of the proper size and shape to support premade ankle hinges 2603. Next, one piece of brace padding 2662 and one brace stiffener 2663 are molded onto substantially the entire cast 130, as shown and described especially in FIG. 18. Preferably, trim lines 2670, as shown, are made by a skilled brace-maker to indicate the correct separation between calf section 2601 and foot section 2602. Preferably, brace stiffener 2663 and brace padding 2662 are then cut and trimmed along the trim lines 2670 and according to the skill of the brace-maker to provide one calf section 2601 and one foot section 2602, as shown.

Figure 26B:
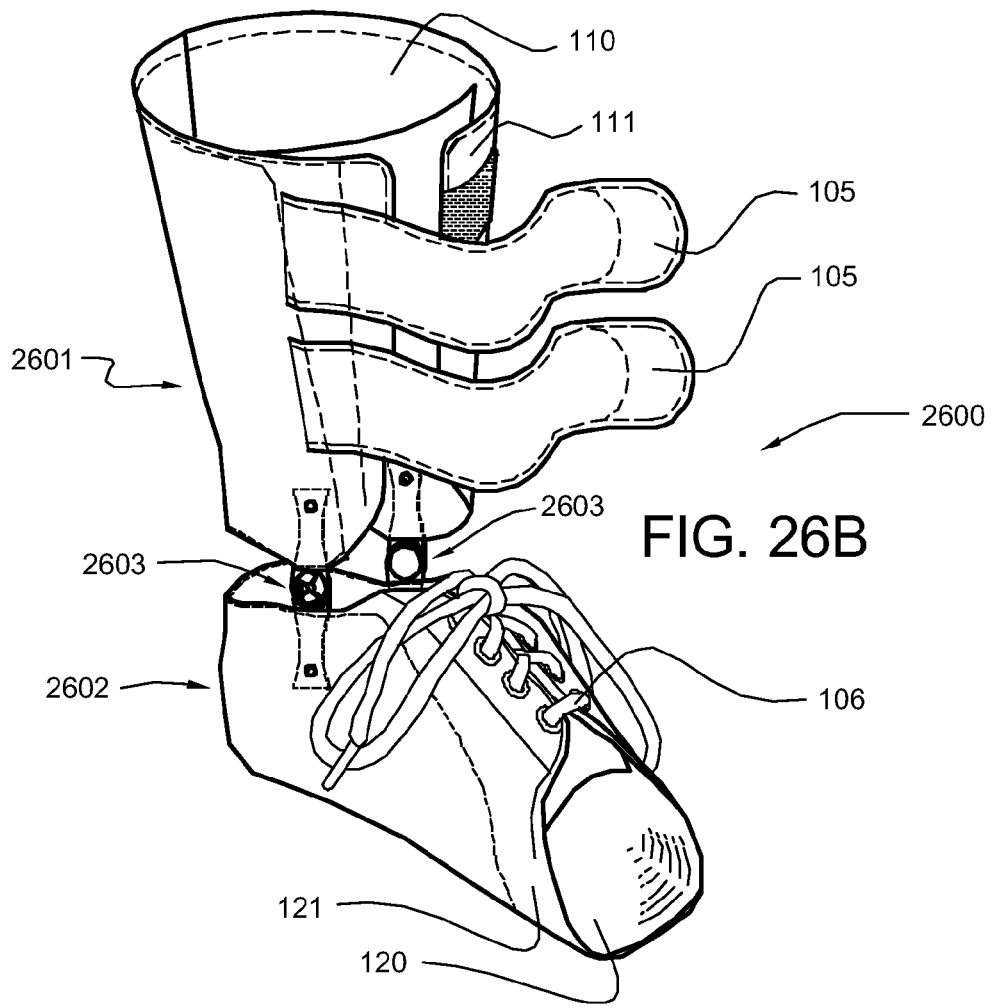
FIG. 26B shows the completed articulated custom AFO system according to FIG. 26A with preferred hinges installed.

Preferably, the buildup 2653 (at least embodying herein the step of making at least one build-up of such at least one positive cast to provide for the placement of such at least one medial hinge and such at least one lateral hinge) on cast 130 is designed to create recesses of the precise size and shape needed to support the premade ankle hinge 2603 and to hold the premade ankle hinge 2603 slightly away from the ankle of the wearer, as shown especially in FIG. 26B. Upon reading the teachings of this specification, those with ordinary skill in the art will now understand that, under appropriate circumstances, considering such issues as user preference, advances in technology, ankle hinge shape, ankle hinge placement, etc., other cast buildup 2653 sizes and shapes sufficient to create a space to support a premade ankle hinge 2603, such as cubic, half-pipe, installing dummy hinges on the cast, etc., may suffice. Upon reading the teachings of this specification, those with ordinary skill in the art will now understand that, under appropriate circumstances, considering such issues as user preference, advances in technology, type of hinge, etc., other hinge placements, such as on the exterior of the calf stiffener 112, on the exterior of the foot stiffener 122, at the rear of the articulated custom AFO 2600, etc., may suffice.

Upon reading the teachings of this specification, those with ordinary skill in the art will now understand that, under appropriate circumstances, considering such issues as advances in technology, user preference, type of hinge, patient needs etc., other steps, such as trimming brace padding away from built-up cast areas prior to molding the brace stiffener, trimming brace padding out of recessed spaces in the stiffener prior to installing premade ankle hinges, etc., may suffice.

FIG. 26B shows the completed articulated custom AFO system 2600, according to FIG. 26A, with premade ankle hinges 2603 installed. In this embodiment, the recessed spaces 2615 and 2625 comprise lateral extensions 115 and 125 and the recessed spaces 2614 and 2624 comprise medial extensions 114 and 124. Upon reading the teachings of this specification, those with ordinary skill in the art will now understand that, under appropriate circumstances, considering such issues as user preference, advances in technology, type of premade ankle hinge, etc., medial extensions and lateral extensions may have other shapes, such as concave, convex, tall, short, etc., which may suffice for supporting premade ankle hinges.

Figure 26C:
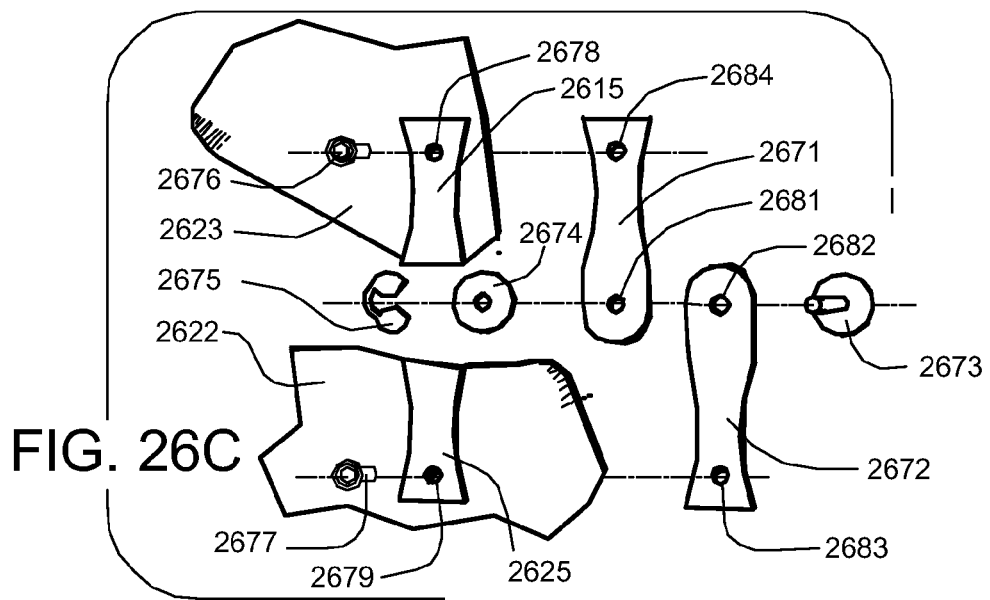
FIG. 26C shows the construction of the preferred hinges of the articulated custom AFO system according to FIG. 26B.

Preferably, premade ankle hinges 2603 are first at least partially installed, as shown and described especially in FIG. 26C, in calf section 2601 and foot section 2602. Preferably, calf inner lining 110, foot inner lining 120, calf outer lining 111, and foot outer lining 121 are cut, sewn, and applied as previously shown and described especially in FIG. 21A through FIG. 22C. Preferably, calf tightener 105 and foot tightener 106 are applied as previously shown and described especially in FIG. 23 and FIG. 24.

FIG. 26C shows an exploded view of preferred hinges 2603 of the articulated custom AFO 2600 according to FIG. 26B. Preferably, calf padding 2612 and foot padding 2623 are peeled away from medial extensions 114 and 124 and lateral extensions 115 and 125 prior to installing premade ankle hinges 2603. Preferably, upper hinge recess hole 2678, as shown, and lower hinge recess hole 2679, as shown, are punched or, more preferably, drilled, in the locations shown. Preferably, upper hinge arm 2671 fits into upper hinge recess 2615, as shown, and is secured with screw 2676 through upper hinge recess hole 2678 and upper hinge arm hole 2684, as shown. Preferably, lower hinge arm 2672 fits into lower hinge recess 2625, as shown, and is secured with screw 2677 through lower hinge recess hole 2679 and lower hinge arm hole 2683, as shown. Preferably, axle bolt 2673 fits through axle hole 2681 in upper hinge arm 2671 and axle hole 2682 in lower hinge arm 2672, as shown. Preferably, washer 2674 and retaining clip 2675 are then installed on axle bolt 2673, as shown.

Preferably, the previously peeled-away portions of calf padding 2612 are re-adhered to calf stiffener 2613 after premade ankle hinges 2603 are installed, so that calf padding 2612 is between the wearer and at least a portion of premade ankle hinges 2603. Preferably, the previously peeled-away portions of foot padding 2623 are re-adhered to foot stiffener 2622 after premade ankle hinges 2603 are installed, so that foot padding 2623 is between the wearer and at least a portion of premade ankle hinges 2603. Preferably, calf inner lining 110, foot inner lining 120, calf outer lining 111, and foot outer lining 121 are applied (as previously shown and described especially in FIG. 21A through FIG. 22C) after premade ankle hinges 2603 are installed, such that calf inner lining 110, foot inner lining 120, calf outer lining 111 preferably cover at least screw 2677 and screw 2676, as shown especially in FIG. 26B. Upon reading the teachings of this specification, those with ordinary skill in the art will now understand that, under appropriate circumstances, considering such issues as user preference, advances in technology, type of hinge, etc., other hinge attachment arrangements, such as padding lying between the hinge and the stiffener, screws extending through the outer lining, screws extending through the inner lining, linings being trimmed away from the hinges, etc., may suffice.

Figure 27A:
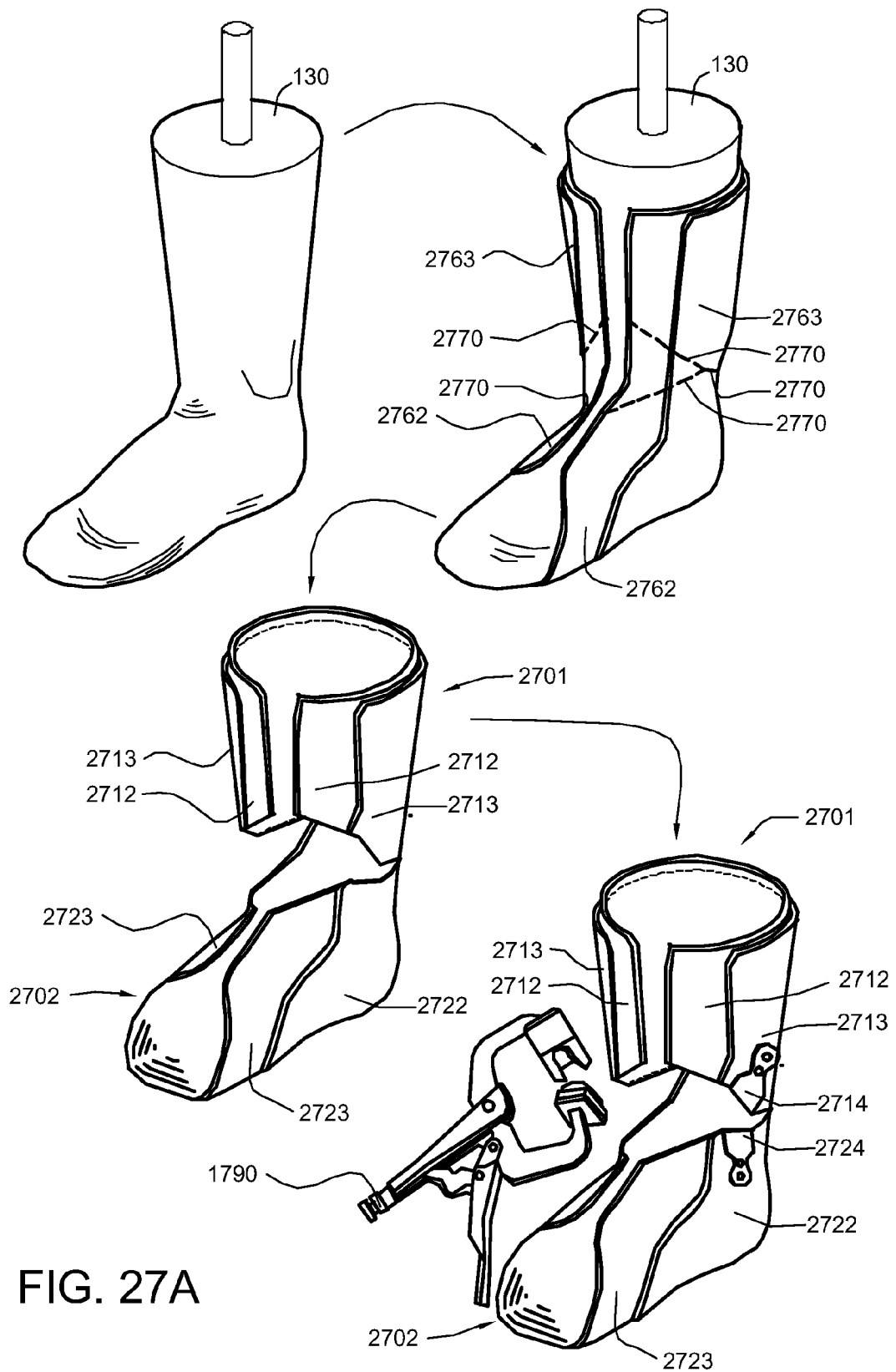
FIG. 27A shows steps in a process of manufacturing an articulated custom AFO system according to a preferred embodiment of the present invention.

FIG. 27A shows steps in a process of manufacturing an articulated custom AFO system 2700 according to a preferred embodiment of the present invention. Preferably, articulated custom AFO 2700 utilizes a premade ankle hinge 2703, such as, for example, Masser ankle hinge model number MG-SAJ1, available from Otto Bock of Minneapolis, Minn., USA, as shown especially in FIG. 27B. Articulated custom AFO 2700 is preferably manufactured in one piece by molding brace stiffener 2763 and brace padding 2762 onto cast 130, cutting brace stiffener 2763 and brace padding 2762 into a calf section 2701 and a foot section 2702, stamping recessed spaces 2714 and 2715 in calf section 2701 and recessed spaces 2724 and 2725 in foot section 2702 of the proper size and shape to support premade ankle hinges 2703, and then installing premade ankle hinges 2703 to hingedly connect calf section 2701 and foot section 2702.

First, one piece of brace padding 2762 and one brace stiffener 2763 are molded onto substantially the entire cast 130, substantially as shown and described especially in FIG. 18. Trim lines 2770 are then made by a skilled brace-maker to indicate the correct separation between calf section 2701 and foot section 2702. Preferably, brace stiffener 2763 and brace padding 2762 are then cut and trimmed along the trim lines 2770 to provide one calf section 2701 and one foot section 2702, as shown. Then, the hinge attachment areas (defined as the intended locations of recessed spaces 2714 and 2715) on calf section 2701 and the hinge attachment areas (defined as the intended locations of recessed spaces 2724 and 2725) on foot section 2702 are re-heated to pliability, preferably with a heat gun. Stamping tool 1790 (at least embodying herein the step of stamping such at least one calf stiffener and such at least one foot stiffener to provide for the placement of such at least one medial hinge and such at least one lateral hinge) is then used to stamp recessed spaces 2724 and 2725 in foot section 2702 and recessed spaces 2714 and 2715 into calf section 2701 to support premade ankle hinges 2703 (recessed spaces 2715 and 2725 are shown not yet stamped). Preferably, stamping tool 1790 is designed to create a recess of the precise size and shape needed to support premade ankle hinges 2703. Upon reading the teachings of this specification, those with ordinary skill in the art will now understand that, under appropriate circumstances, considering such issues as user preference, advances in technology, ankle hinge shape, ankle hinge placement, etc., other stamp sizes and shapes sufficient to create a space to support an ankle hinge, such as cubic, half-pipe, dummy-hinge shaped, etc., may suffice. Upon reading the teachings of this specification, those with ordinary skill in the art will now understand that, under appropriate circumstances, considering such issues as user preference, advances in technology, type of hinge, etc., other hinge placements, such as on the exterior of the calf stiffener, on the exterior of the foot stiffener, at the rear of the articulated custom AFO, etc., may suffice.

Upon reading the teachings of this specification, those with ordinary skill in the art will now understand that, under appropriate circumstances, considering such issues as advances in technology, user preference, etc., other steps, such as temporarily peeling the calf padding away from the calf stiffener prior to using the stamping tool on the calf stiffener, trimming the calf padding away from the hinge attachment areas prior to using the stamping tool, trimming the calf padding out of the recessed spaces prior to installing the premade ankle hinges, temporarily peeling the foot padding away from the foot stiffener prior to using the stamping tool on the foot stiffener, trimming the foot padding away from the hinge attachment areas prior to using the stamping tool, trimming the foot padding out of the recessed spaces prior to installing the premade ankle hinges, etc., may suffice.

Figure 27B:
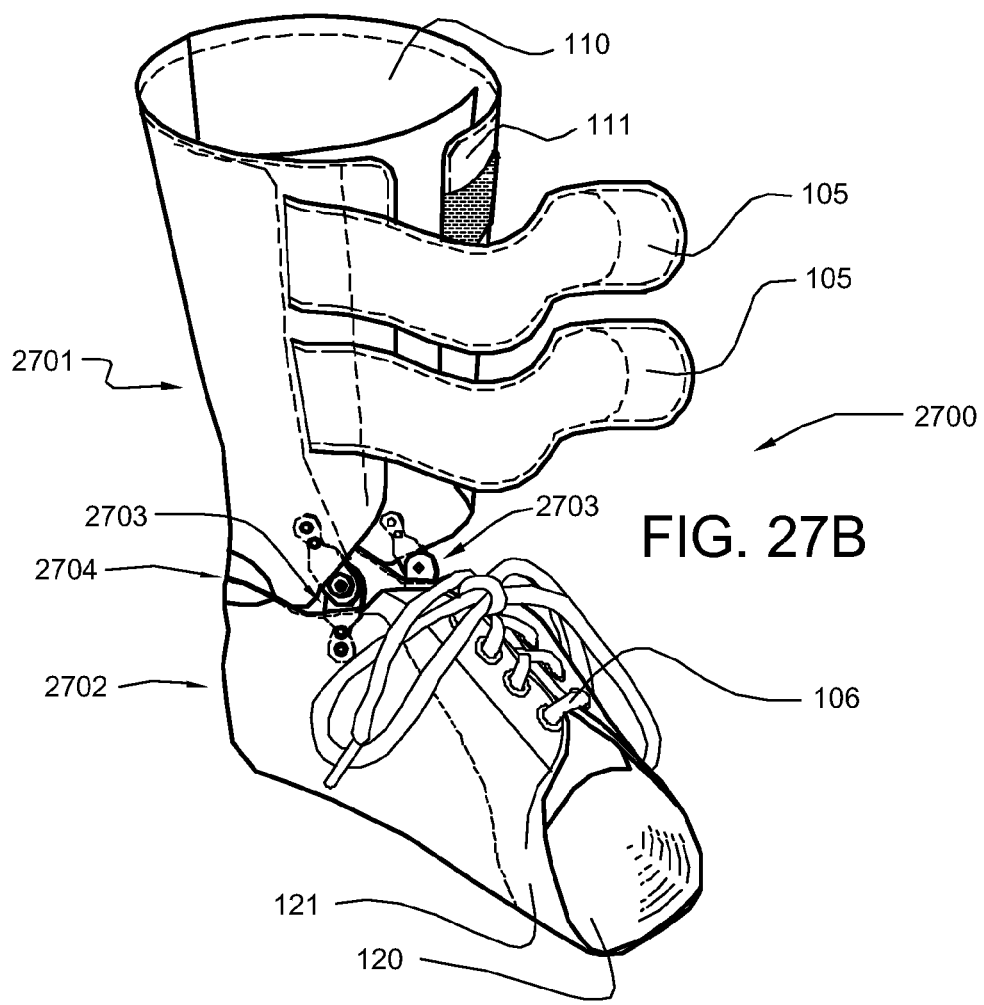
FIG. 27B shows the completed articulated custom AFO system according to FIG. 27A with preferred hinges installed.

FIG. 27B shows the completed articulated custom AFO system 2700 with premade ankle hinges 2703 installed. In this embodiment, the recessed spaces 2715 and 2725 comprise lateral extensions 115 and 125 and recessed spaces 2714 and 2724 comprise medial extensions 114 and 124. Upon reading the teachings of this specification, those with ordinary skill in the art will now understand that, under appropriate circumstances, considering such issues as user preference, advances in technology, type of premade ankle hinge, etc., the medial extensions and the lateral extensions may have other shapes, such as concave, convex, tall, short, etc., which may suffice for supporting the hinges.

Calf inner lining 110, foot inner lining 120, calf outer lining 111, and foot outer lining 121 are cut, sewn, and applied, substantially as previously shown and described especially in FIG. 21A through FIG. 22C. Calf tightener 105 and foot tightener 106 are applied, substantially as previously shown and described especially in FIG. 23 and FIG. 24.

Preferably, articulated custom AFO 2700 comprises backstop 2704, as shown, to assist wearers who have difficulty lifting the front portion of the foot during walking. Preferably, backstop 2704 (at least embodying herein backstop means for stopping such foot portion from moving past a certain angle relative to such calf portion) causes foot section 2702 to impact calf section 2701 at the rear of articulated custom AFO 2700 when foot section 2702 attempts to make an angle greater than 90 degrees (or other desired stop angle, as medically appropriate) with respect to calf section 2701, as shown. Backstop 2704 is preferably reinforced and thickened with extra thermoplastic (as shown) during the stiffener molding process (shown and described in FIG. 18) to create a larger and stronger impact area. Upon reading the teachings of this specification, those with ordinary skill in the art will now understand that, under appropriate circumstances, considering such issues as user preference, advances in technology, desired stop angle, etc., other backstops, such as adjustable backstops, removable backstops, other backstop shapes, etc., may suffice.

Figure 27C:
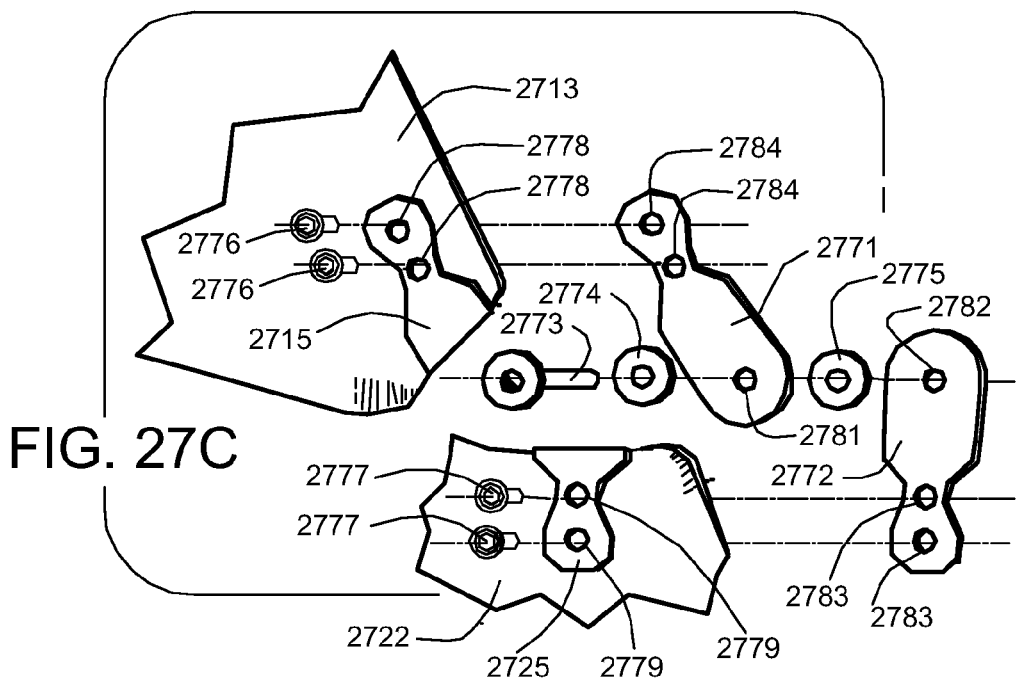
FIG. 27C shows an exploded view of the preferred hinges of the articulated custom AFO system according to FIG. 27B.

FIG. 27C shows an exploded view of preferred hinges 2703 of articulated custom AFO system 2700 according to FIG. 27B. Preferably, calf padding 2712 and foot padding 2723 are peeled away from medial extensions 114 and 124 and lateral extensions 115 and 125 prior to installing hinges 2703. Preferably, upper hinge recess holes 2778, as shown, and lower hinge recess holes 2779, as shown, are punched or, more preferably, drilled, prior to installing premade ankle hinges 2703. Preferably, upper hinge arm 2771 fits into upper hinge recess 2715, as shown, and is secured with screws 2776 through upper hinge recess holes 2778 and upper hinge arm holes 2784, as shown. Preferably, lower hinge arm 2772 fits into lower hinge recess 2725, as shown, and is secured with screws 2777 through lower hinge recess holes 2779 and lower hinge arm holes 2783, as shown. Preferably, axle bolt 2773 fits through washer 2774, axle hole 2781 in upper hinge arm 2771, washer 2775, and axle hole 2782 in lower hinge arm 2772, as shown.

Preferably, the previously peeled-away portions of calf padding 2712 are re-adhered to calf stiffener 2713 after premade ankle hinges 2703 are installed, so that calf padding 2712 is between the wearer and at least a portion of premade ankle hinges 2703. Preferably, the previously peeled-away portions of foot padding 2723 are re-adhered to foot stiffener 2722 after premade ankle hinges 2703 are installed, so that foot padding 2723 is between the wearer and at least a portion of premade ankle hinges 2703. Preferably, calf inner lining 110, foot inner lining 120, calf outer lining 111, and foot outer lining 121 are applied (as previously shown and described especially in FIG. 21A through FIG. 22C) after premade ankle hinges 2703 are installed, such that calf inner lining 110, foot inner lining 120, calf outer lining 111 preferably cover at least screws 2776 and screws 2777, as shown especially in FIG. 27B. Upon reading the teachings of this specification, those with ordinary skill in the art will now understand that, under appropriate circumstances, considering such issues as user preference, advances in technology, type of hinge, etc., other hinge attachment arrangements, such as padding lying between the hinge and the stiffener, screws extending through the outer lining, screws extending through the inner lining, linings being trimmed away from the hinges, etc., may suffice.

Figure 28A:
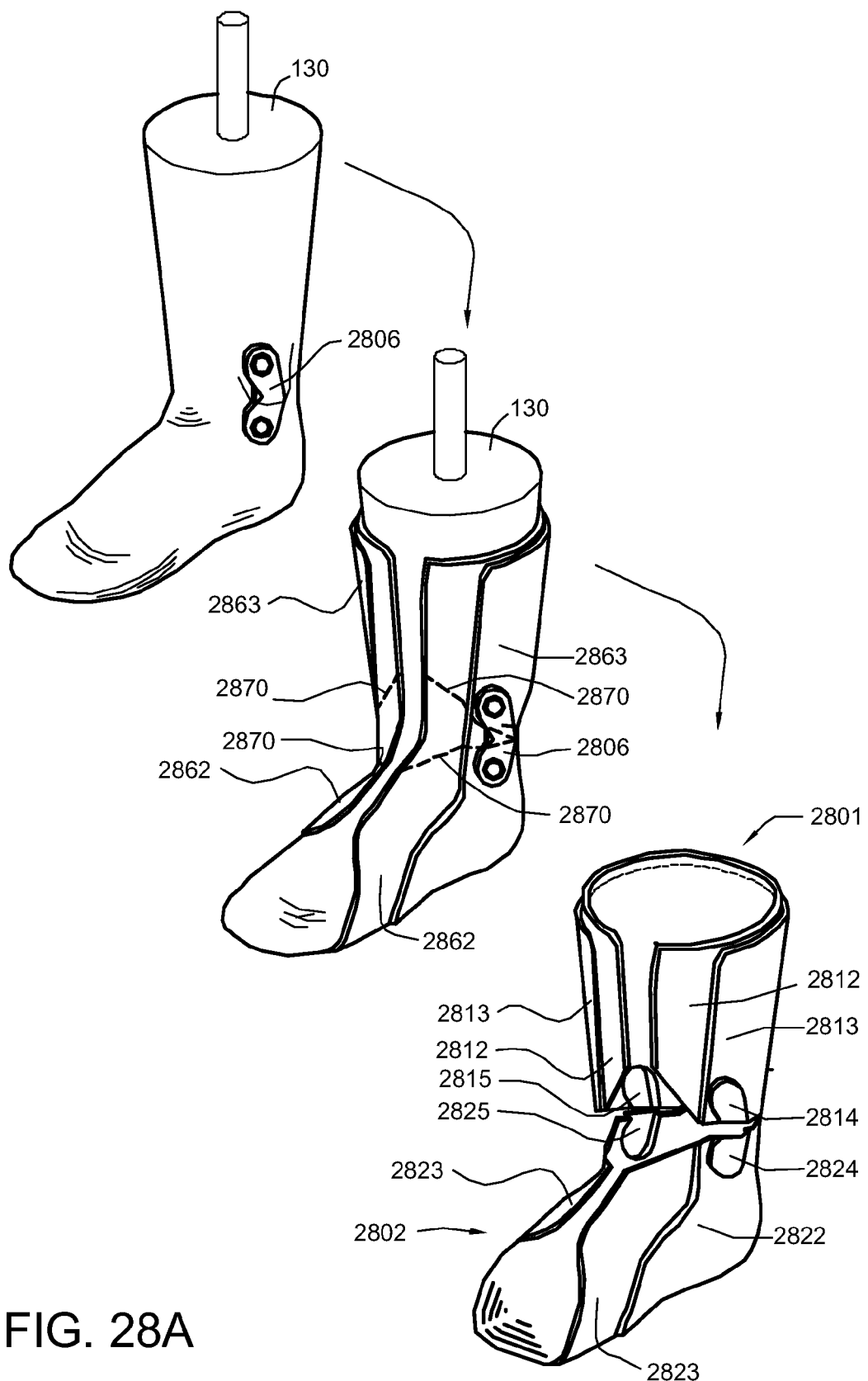
FIG. 28A shows steps in a process of manufacturing an articulated custom AFO system according to a preferred embodiment of the present invention

FIG. 28A shows steps in a process of manufacturing an articulated custom AFO system 2800 according to a preferred embodiment of the present invention. Preferably, articulated custom AFO 2800 utilizes a premade ankle hinge 2803, such as, for example, Tamarack ankle hinge model number 740, Michigan, USA, as shown especially in FIG. 28B. Articulated custom AFO 2800 is preferably manufactured in one piece by placing molding dummies 2806 onto cast 130, molding brace stiffener 2863 (at least embodying herein making at least one brace stiffener for use within such at least one material layers in making such at least one ankle-foot orthosis for such patient) and brace padding 2862 onto cast 130, cutting brace stiffener 2863 and brace padding 2862 into a calf section 2801 and a foot section 2802, and then installing premade ankle hinges 2803 to hingedly connect calf section 2801 and foot section 2802.

Molding dummies 2806 are preferably sized and shaped to create recessed spaces 2814 and 2815 in calf section 2801 and recessed spaces 2824 and 2825 in foot section 2802 of the proper size and shape to support premade ankle hinges 2803. First, molding dummies 2806 (at least embodying herein the step of placing at least one molding dummy on such at least one positive cast to provide for the placement of such at least one medial hinge and such at least one lateral hinge) are preferably placed in the correct location on cast 130, as shown, according to the skill of the brace-maker. Then, one piece of brace padding 2862 and one brace stiffener 2863 are molded onto substantially the entire cast 130, substantially as shown and described especially in FIG. 18. Preferably, trim lines 2870, as shown, are then made by a skilled brace-maker to indicate the correct separation between calf section 2801 and foot section 2802. Preferably, brace stiffener 2863 and brace padding 2862 are then cut and trimmed along the trim lines 2870 and according to the skill of the brace-maker to provide one calf section 2801 and one foot section 2802, as shown.

Preferably, the two molding dummies 2806 are designed to create recesses of the precise size and shape needed to support the premade ankle hinge 2803 and to hold the premade ankle hinge 2803 slightly away from the ankle of the wearer, as shown especially in FIG. 28B. Upon reading the teachings of this specification, those with ordinary skill in the art will now understand that, under appropriate circumstances, considering such issues as user preference, advances in technology, ankle hinge shape, ankle hinge placement, etc., other molding dummy sizes and shapes sufficient to create a space to support an ankle hinge, such as cubic, half-pipe, etc., may suffice. Upon reading the teachings of this specification, those with ordinary skill in the art will now understand that, under appropriate circumstances, considering such issues as user preference, advances in technology, type of hinge, etc., other hinge placements, such as on the exterior of the calf stiffener, on the exterior of the foot stiffener, at the rear of the articulated custom AFO, etc., may suffice.

Upon reading the teachings of this specification, those with ordinary skill in the art will now understand that, under appropriate circumstances, considering such issues as advances in technology, user preference, patient needs, etc., other steps, such as building up the cast to provide additional support for the molding dummies, applying the molding dummies to the cast after the step of molding the brace padding and before the step of molding the brace stiffener, trimming calf padding and foot padding out of the recessed spaces prior to installing the premade ankle hinges, etc., may suffice.

FIG. 28B shows the completed articulated custom AFO system 2800 according to FIG. 28A, with premade ankle hinges 2803 installed. In this embodiment, the recessed spaces 2815 and 2825 created by one molding dummy 2806 comprise the lateral extensions 115 and 125 and the recessed spaces 2814 and 2824 created by the other molding dummy 2806 comprise the medial extensions 114 and 124. Upon reading the teachings of this specification, those with ordinary skill in the art will now understand that, under appropriate circumstances, considering such issues as user preference, advances in technology, type of premade ankle hinge, etc., medial and lateral extensions may have other shapes, such as concave, convex, tall, short, etc., which may suffice for supporting the premade ankle hinges.

Calf inner lining 110, foot inner lining 120, calf outer lining 111, and foot outer lining 121 are cut, sewn, and applied substantially as previously shown and described especially in FIG. 21A through FIG. 22C. Calf tightener 105 and foot tightener 106 are applied substantially as previously shown and described especially in FIG. 23 and FIG. 24.

FIG. 28C shows an exploded view of preferred hinges 2803 of articulated custom AFO system 2800 according to FIG. 28B. Preferably, calf padding 2812 and foot padding 2823 are peeled away from medial extensions 114 and 124 and lateral extensions 115 and 125 prior to installing premade ankle hinges 2803. Preferably, upper hinge recess hole 2878, as shown, and lower hinge recess hole 2879, as shown, are punched or, more preferably, drilled, prior to installing premade ankle hinges 2803. Preferably, screw 2876 goes through upper hinge recess hole 2878 in upper hinge recess 2815, through top hole 2884 of flexure joint 2893, and into bushing 2885. Preferably, screw 2877 goes through lower hinge recess hole 2879 in lower hinge recess 2825, through bottom hole 2883 of flexure joint 2893, and into bushing 2882.

Preferably, the previously peeled-away portions of calf padding 2812 are re-adhered to calf stiffener 2813 after premade ankle hinges 2803 are installed, so that calf padding 2812 is between the wearer and at least a portion of premade ankle hinges 2803. Preferably, the previously peeled-away portions of foot padding 2823 are re-adhered to foot stiffener 2822 after premade ankle hinges 2803 are installed, so that foot padding 2823 is between the wearer and at least a portion of premade ankle hinges 2803. Preferably, calf inner lining 110, foot inner lining 120, calf outer lining 111, and foot outer lining 121 are applied (as previously shown and described especially in FIG. 21A through FIG. 22C) after premade ankle hinges 2803 are installed, such that calf inner lining 110, foot inner lining 120, calf outer lining 111 preferably cover at least screw 2876, bushing 2885, screw 2877, and bushing 2882, as shown especially in FIG. 28B. Upon reading the teachings of this specification, those with ordinary skill in the art will now understand that, under appropriate circumstances, considering such issues as user preference, advances in technology, type of hinge, etc., other hinge attachment arrangements, such as padding lying between the hinge and the stiffener, screws extending through the outer lining, screws extending through the inner lining, linings being trimmed away from the hinges, etc., may suffice.

FIG. 29 shows a completed articulated custom AFO 100 with an essentially normal shoe 126. Essentially normal shoe 126 is preferably used with articulated custom AFO 100 because the hinge hardware does not extend very far into essentially normal shoe 126, if at all. Articulated custom AFO 100 has outer surfaces that are compatible with the inner surfaces of the essentially normal shoe 126.

FIG. 30A shows plantar/dorsal pivot point 127 of an ankle 128. Pivot point 127 will vary with each patient, and is preferably marked on stockinette 145. In cases of injury or deformity, the pivot point 127 may be significantly displaced, but the methods for producing articulated custom AFO 100 remain the same.

FIG. 30B shows the plantar/dorsal pivot point 127 of the completed articulated custom AFO 100, which preferably aligns with plantar/dorsal pivot point 127 of ankle 128.

Although applicant has described applicant's preferred embodiments of this invention, it will be understood that the broadest scope of this invention includes such modifications as diverse shapes and sizes and materials. Such scope is limited only by the below claims as read in connection with the above specification. Further, many other advantages of applicant's invention will be apparent to those skilled in the art from the above descriptions and the below claims.

What is claimed is:

1. An articulated custom AFO system, for permitting dorsal and plantar ankle flexion between a calf and a foot of at least one lower leg of at least one user, comprising:
   a) at least one calf portion, having inside and outside surfaces;
   b) at least one foot portion, having inside and outside surfaces;
   c) at least one calf stiffener, having medial and lateral sides and inside and outside surfaces, structured and arranged to stiffly support said at least one calf portion;
   d) at least one foot stiffener, having medial and lateral sides and inside and outside surfaces, structured and arranged to stiffly support said at least one foot portion;
   e) at least one medial hinge structured and arranged to hingedly connect said medial side of said at least one calf stiffener to said medial side of said at least one foot stiffener;
   f) at least one lateral hinge structured and arranged to hingedly connect said lateral side of said at least one calf stiffener to said lateral side of said at least one foot stiffener;
   g) at least one calf outer lining structured and arranged to pliably line at least said outside surface of said at least one calf stiffener;
   h) at least one foot outer lining structured and arranged to pliably line at least said outside surface of said at least one foot stiffener;
   i) at least one calf tightener structured and arranged to tighten said at least one calf outer lining about the calf of the at least one user; and
   j) at least one attacher structured and arranged to attach said at least one calf tightener with said at least one calf outer lining;
   k) wherein said at least one calf portion comprises at least one circumferential lower-leg support structured and arranged to circumferentially-support, by substantially encircling, the at least one lower leg of the at least one user, when worn.

2. The articulated custom AFO system, according to claim 1, wherein said at least one foot portion comprises arch support structured and arranged to provide support to arch of the foot of the at least one user, when worn.

3. The articulated custom AFO system, according to claim 2, wherein said at least one arch support comprises midfoot-and-heel-encircling support structured and arranged to substantially encircle midfoot and heel of the foot of the at least one user, providing support to the arch of the foot, when worn.

4. The articulated custom AFO system, according to claim 1, wherein said at least one medial hinge comprises at least one rivet hinge.

5. The articulated custom AFO system, according to claim 1, wherein said at least one medial hinge comprises at least one pre-made medial ankle hinge.

6. The articulated custom AFO system, according to claim 1, wherein said at least one lateral hinge comprises at least one rivet hinge.

7. The articulated custom AFO system, according to claim 1, wherein said at least one lateral hinge comprises at least one pre-made ankle hinge.

8. The articulated custom AFO system, according to claim 1, further comprising at least one foot tightener structured and arranged to tighten said at least one foot outer liner about the foot of the at least one user.

9. The articulated custom AFO system, according to claim 8, wherein said at least one foot tightener comprises at least one grommet and at least one lace.

10. The articulated custom AFO system, according to claim 8, further comprising at least one foot tongue structured and arranged to cover the area at least under said at least one foot tightener.

11. The articulated custom AFO system, according to claim 1, further comprising at least one calf tongue structured and arranged to cover the area at least under said at least one calf tightener.

12. The articulated custom AFO system, according to claim 1, wherein said at least one calf tightener comprises at least one hook and loop fastener.

13. The articulated custom AFO system, according to claim 1, further comprising at least one backstop structured and arranged to stop said at least one foot portion from moving past at least one angle relative to said at least one calf portion.

14. An articulated custom AFO system, for permitting dorsal and plantar ankle flexion between a calf and a foot of at least one lower-leg of at least one user, comprising:
  a) at least one calf portion, having inside and outside surfaces;
  b) at least one foot portion, having inside and outside surfaces;
  c) calf stiffener means, having medial and lateral sides and inside and outside surfaces, for stiffly supporting said at least one calf portion;
  d) foot stiffener means, having medial and lateral sides and inside and outside surfaces, for stiffly supporting said at least one foot portion;
  e) medial hinge means for hingedly connecting said medial side of said calf stiffener means to said medial side of said foot stiffener means;
  f) lateral hinge means for hingedly connecting said lateral side of said calf stiffener means to said lateral side of said foot stiffener means;
  g) calf outer lining means for pliably lining at least said outside surface of said calf stiffener means;
  h) foot outer lining means for pliably lining at least said outside surface of said foot stiffener means;
  i) calf tightener means for tightening said calf outer lining means about the calf of the at least one user; and
  j) attachment means for attaching said calf tightener means with said calf outer lining means;
  k) wherein said at least one calf portion comprises circumferential lower-leg support means for circumferentially-supporting, by substantially encircling, the at least one lower leg of the at least one user, when worn.

15. The articulated custom AFO system, according to claim 14, wherein said at least one foot portion comprises arch support means for providing support to arch of the foot of the at least one user, when worn.

16. The articulated custom AFO system, according to claim 15, wherein arch support means comprises midfoot-and-heel encircling means for substantially encircling of midfoot and heel of the foot of the at least one user, when worn.

17. The articulated custom AFO system, according to claim 14, further comprising backstop means for stopping said foot portion from moving past a certain angle relative to said calf portion.

18. The articulated custom AFO system, according to claim 14, wherein said foot outer lining means substantially covers the outer surfaces of said medial hinge means and said lateral hinge means.

19. A method of making at least one custom articulated custom AFO system, for permitting dorsal and plantar ankle flexion between a calf and a foot of at least one lower leg of at least one user, comprising the steps of:
  a) making at least one custom articulated AFO, specifically corresponding to a foot-ankle-calf structure of a specific individual;
  b) making at least one outer calf lining;
  c) making at least one outer foot lining;
  d) attaching such at least one calf outer lining to such at least one custom articulated AFO; and
  e) attaching such at least one foot outer lining to such at least one custom articulated AFO;
  f) wherein said at least one custom articulated AFO comprises
    i) at least one calf portion, having inside and outside surfaces;
    ii) at least one foot portion, having inside and outside surfaces;
    iii) at least one calf stiffener, having medial and lateral sides and inside and outside surfaces, structured and arranged to stiffly support said at least one calf portion;
    iv) at least one foot stiffener, having medial and lateral sides and inside and outside surfaces, structured and arranged to stiffly support said at least one foot portion;
    v) at least one medial hinge structured and arranged to hingedly connect said medial side of said at least one calf stiffener to said medial side of said at least one foot stiffener;
    vi) at least one lateral hinge structured and arranged to hingedly connect said lateral side of said at least one calf stiffener to said lateral side of said at least one foot stiffener;
    vii) at least one calf outer lining structured and arranged to pliably line at least said outside surface of said at least one calf stiffener;
    viii) at least one foot outer lining structured and arranged to pliably line at least said outside surface of said at least one foot stiffener;
    ix) at least one calf tightener structured and arranged to tighten said at least one calf outer lining about the calf of the at least one user; and
    x) at least one attacher structured and arranged to attach said at least one calf tightener with said at least one calf outer lining;
    xi) wherein said at least one calf portion comprises at least one circumferential lower-leg support structured and arranged to circumferentially-support, by substantially encircling, the at least one lower leg of the at least one user, when worn has been inserted.

* * * * *

UNITED STATES PATENT AND TRADEMARK OFFICE
CERTIFICATE OF CORRECTION

PATENT NO. : 8,048,012 B1  
APPLICATION NO. : 12/708434  
DATED : November 1, 2011  
INVENTOR(S) : Ernesto G. Castro Page 1 of 1

It is certified that error appears in the above-identified patent and that said Letters Patent is hereby corrected as shown below:

Column 26, Claim 19, line 64, "when worn, has been inserted." should read --when worn.--

Signed and Sealed this
Thirty-first Day of January, 2012

David J. Kappos
*Director of the United States Patent and Trademark Office*